(12) United States Patent
Nomura et al.

(10) Patent No.: US 8,221,904 B2
(45) Date of Patent: Jul. 17, 2012

(54) OXADIAZOLE DERIVATIVE AND LIGHT-EMITTING ELEMENT, LIGHT-EMITTING DEVICE, AND ELECTRONIC DEVICE IN WHICH THE OXADIAZOLE DERIVATIVE IS USED

(75) Inventors: Hiroko Nomura, Isehara (JP); Satoshi Seo, Kawasaki (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 411 days.

(21) Appl. No.: 12/076,452

(22) Filed: Mar. 19, 2008

(65) Prior Publication Data

US 2008/0230747 A1    Sep. 25, 2008

(30) Foreign Application Priority Data

Mar. 20, 2007   (JP) .................. 2007-072624

(51) Int. Cl.
*H01L 51/54* (2006.01)
(52) U.S. Cl. ......... 428/690; 428/917; 313/504; 313/506
(58) Field of Classification Search .......... None
See application file for complete search history.

(56) References Cited

U.S. PATENT DOCUMENTS 5,420,288 A * 5/1995 Ohta et al. .......... 548/145
(Continued)

FOREIGN PATENT DOCUMENTS
CN        1854136        11/2006
(Continued)

OTHER PUBLICATIONS

Organic Letters, (2009), vol. 11, No. 14, pp. 3072-3075.*
(Continued)

*Primary Examiner* — Dawn L. Garrett
(74) *Attorney, Agent, or Firm* — Eric J. Robinson; Robinson Intellectual Property Law Office, P.C.

(57) ABSTRACT

The object of the present invention is to provide a material that has a high excitation energy, in particular, a high triplet excitation energy. Furthermore, another object of the present invention is to provide a material than can be easily synthesized and that has low crystallinity. In addition, another object of the present invention is to provide a light-emitting element that has high luminous efficacy and high reliability by application of this material to the light-emitting element. An oxadiazole derivative represented by the General Formula (G1) given below is synthesized and applied to a light-emitting element.

[Chemical Formula: General Formula (G1)]

($R^1$ to $R^7$ each represent either hydrogen or an alkyl group with from 1 to 4 carbon atoms).

14 Claims, 8 Drawing Sheets

U.S. PATENT DOCUMENTS

| | | | |
|---|---|---|---|
| 5,610,309 A | 3/1997 | Ohta et al. | |
| 6,285,039 B1* | 9/2001 | Kobori et al. | 257/40 |
| 6,329,084 B1 | 12/2001 | Tamano et al. | |
| 6,593,013 B2 | 7/2003 | Nii et al. | |
| 6,784,318 B2 | 8/2004 | Shirota et al. | |
| 6,797,848 B2 | 9/2004 | Hosokawa et al. | |
| 7,038,086 B2 | 5/2006 | Shirota et al. | |
| 2002/0093005 A1* | 7/2002 | Sohn et al. | 252/301.16 |
| 2005/0031899 A1* | 2/2005 | Nomura et al. | 428/690 |
| 2005/0127826 A1* | 6/2005 | Qiu et al. | 313/504 |
| 2006/0134456 A1* | 6/2006 | Ikeda et al. | 428/690 |
| 2007/0222376 A1* | 9/2007 | Ohsawa et al. | 313/506 |
| 2008/0149923 A1* | 6/2008 | Ohsawa et al. | 257/40 |

FOREIGN PATENT DOCUMENTS

| | | |
|---|---|---|
| CN | 1919842 | 2/2007 |

OTHER PUBLICATIONS

Baldo et al., "Very High-Efficiency Green Organic Light-Emitting Devices Based on Electrophosphorescence," Applied Physics Letters, Jul. 5, 1999, vol. 75, No. 1, pp. 4-6.

Leung M. et al., The Unusual Electrochemical and Photophysical Behavior of 2,2'—Bis(1,3,4-Oxadiazol-2-yl)Biphenyls, Effective Electron Transport Hosts for Phosphorescent Organic Light Emitting Diodes, Organic Letters, 2007, vol. 9, No. 2, pp. 235-238.

Guan M. et al., High-Performance Blue Electroluminescent Devices Based on 2-(4-Biphenylyl)-5-(4-Carbazole-9-yl)Phenyl-1,3,4-Oxadiazole, Chemical Communication, 2003, pp. 2708-2709.

Search Report (Application No. 08005224.4) dated Jul. 17, 2008.

* cited by examiner

OXADIAZOLE DERIVATIVE AND LIGHT-EMITTING ELEMENT, LIGHT-EMITTING DEVICE, AND ELECTRONIC DEVICE IN WHICH THE OXADIAZOLE DERIVATIVE IS USED

BACKGROUND OF THE INVENTION

1. Field of the Invention

The present invention relates to oxadiazole derivatives. Furthermore, the invention relates to light-emitting elements, light-emitting devices, and electronic devices in which oxadiazole derivatives are used.

2. Description of the Related Art

There is a greater variety in types of organic compounds compared to inorganic compounds, and materials that have a variety of different functions can be designed and synthesized. Because of these types of advantages, attention has been focused on electronics devices in which organic compounds are used in recent years. For example, solar cells, light-emitting elements, transistors, and the like in which organic compounds are used as functional materials are some typical examples of these electronics devices.

These electronics devices are devices that use the electrical properties and optical properties of organic compounds; of these devices, in particular, research and development of light-emitting elements in which organic compounds are used as luminescent materials has been showing an impressive amount of progress.

The structure of these light-emitting elements is a simple structure in which only a light-emitting layer that contains an organic compound, which is a luminescent material, is provided between electrodes, and these light-emitting elements have been attracting attention as elements of next-generation flat panel display panels for having the characteristics of being thin and light-weight, having high-speed response, using low direct current low voltage driving, and the like. Furthermore, displays in which these light-emitting elements are used also have the characteristics of having superior contrast and image quality and having a wide viewing angle.

The light-emitting mechanism of the light-emitting elements in which organic compounds are used as the luminescent material is carrier injection. That is, by application of a voltage to a light-emitting layer that is interposed between electrodes, holes and electrons injected from the electrodes recombine to place the luminescent material into an excited state, and the luminescent material emits light when the luminescent material returns to the ground state from the excited state. For types of excited states, there is the singlet excited state ($S^*$) and the triplet excited state ($T^*$). In addition, it is thought that the statistical generation ratio of the two states in a light-emitting element is $S^*:T^*=1:3$.

For compounds that emit light when the material returns to the ground state from the singlet excited state (hereinafter, these compounds will be referred to as fluorescent compounds) at room temperature, no emission of light from the triplet excited state (emission of light by phosphorescence) is observed, and only emission of light from the singlet excited state (emission of light by fluorescence) is observed. Consequently, the logical limitation on the internal quantum efficiency (the ratio of the number of photons generated with respect to the number of carriers injected) in a light-emitting element in which a fluorescent compound is used is regarded as being 25%, based on $S^*:T^*=1:3$.

On the other hand, if compounds that emit light when the material returns to the ground state from the triplet excited state (hereinafter, these compounds will be referred to as phosphorescent compounds) are used, the internal quantum efficiency could theoretically be from 75% to 100%. That is to say, a luminous efficacy of phosphorescent compounds could be three to four times as great as that of fluorescent compounds. For these kinds of reasons, for the realization of high-efficiency light-emitting elements, development of light-emitting elements in which phosphorescent compounds are used is being actively carried out in recent years (referring to Non-Patent Document 1 for examples).

When the light-emitting layer of a light-emitting element is formed using one of the aforementioned phosphorescent compounds, for suppression of the concentration quenching of the phosphorescent compound and the quenching due to triplet-triplet annihilation, there are many cases in which the light-emitting layer is formed so that the phosphorescent compound is dispersed throughout a matrix formed of another material. In this case, the material used to form the matrix is called a host material, and the material dispersed throughout the matrix like the phosphorescent material is called a guest material.

When a phosphorescent compound is used for the guest material, a property required of the host material is that the host material have a greater triplet excitation energy (the difference in energy between the ground state and the triplet excited state) than that of the phosphorescent compound. CBP, which is used as the host material in Non-Patent Document 1, is known to have a greater triplet excitation energy than a phosphorescent compound that exhibits emission of light of a green to red color and is widely used as a host material with the phosphorescent compound.

[Non-Patent Document 1] M. A. Baldo et al., *Applied Physics Letters* 75, no. 1 (1999): 4-6.

SUMMARY OF THE INVENTION

A compound like CBP that as a high triplet excitation energy (the difference in energy between the ground state and the triplet excited state) is useful as a host material with a phosphorescent compound.

Furthermore, because the singlet excitation energy (the difference in energy between the ground state and the singlet excited state) is greater than the triplet excitation energy, a material that has a high triplet excitation energy will also have a high singlet excitation energy. Consequently, a material that has a high triplet excitation energy is also useful in a light-emitting element formed using a fluorescent compound as the luminescent material.

However, generally, rod-shaped molecules like CBP have a high level of crystallinity, and a problem exists in that it is difficult to maintain the amorphous state of a film. Application of a material that has a low level of amorphousness to the light-emitting element has adverse effects on the reliability of the light-emitting element because short circuits come to be readily produced in elements in which such materials have been applied.

From the above points, an object of the present invention is to provide materials that have high excitation energies, in particular, high triplet excitation energies. In addition, an object of the present invention is to provide materials that are easy to synthesize and that have low crystallinity.

Moreover, an object of the present invention is to provide light-emitting elements that have high luminous efficacy by application of these types of materials. In addition, an object of the present invention is to provide light-emitting elements that have high reliability.

Furthermore, an object of the present invention is to provide light-emitting devices that have high reliability and low power consumption by fabrication of light-emitting devices in which the aforementioned light-emitting elements are used. Moreover, an object of the present invention is to provide electronic devices that have high reliability and low power consumption by application of these light-emitting devices to the electronic devices.

As the results of repeated committed studies, the present inventors developed an oxadiazole derivative that is represented by the General Chemical Formula (G1), that is, by (G1-1) or (G1-2), which are all given hereinafter, as a solution to the problems. Consequently, one structure of the present invention is the oxadiazole derivative represented by the General Formula (G1), that is, by (G1-1) or (G1-2), which are all given below.

[Chemical Formulas 1: General Formulas (G1), (G1-1), and (G1-2)]

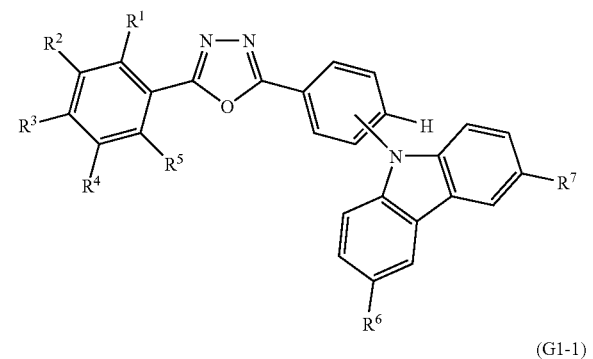

($R^1$ to $R^7$ each represent either hydrogen or an alkyl group that has from 1 to 4 carbon atoms.)

In addition, for a high triplet excitation energy to be obtained and, concurrently, synthesis to be performed easily, use of the oxadiazole derivative represented by the General Formula (G2) given below is favorable.

[Chemical Formula 2: General Formula (G2)]

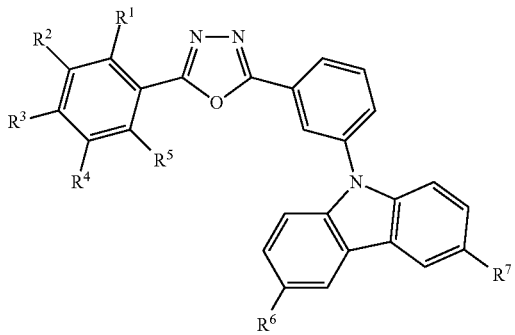

($R^1$ to $R^7$ each represent either hydrogen or an alkyl group that has from 1 to 4 carbon atoms.)

In particular, even within the General Formula (G2), use of the oxadiazole derivative represented by the Structural Formula (1) given below is favorable.

[Chemical Formula 3: Structural Formula (1)]

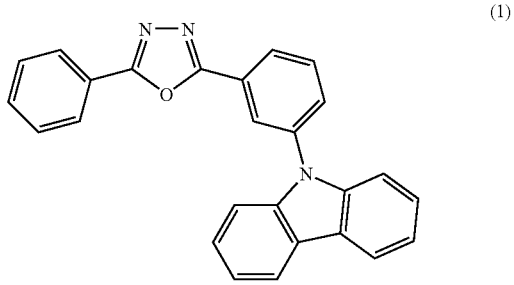

It is to be noted that, in the oxadiazole derivatives of the present invention represented by the General Formulas (G1) and (G2), for the alkyl group that has from 1 to 4 carbon atoms, a methyl group, an ethyl group, an isopropyl group, an isobutyl group, a tert-butyl group, and the like can be given.

Because the oxadiazole derivatives of the present invention represented by the General Formulas (G1) and (G2) and the Structural Formula (1) given above are luminescent, they can be employed in light-emitting elements. Consequently, another structure of the present invention is a light-emitting element that contains any of the oxadiazole derivatives described above.

In addition, because each of the oxadiazole derivatives of the present invention has a high excitation energy and the level of amorphousness of a film formed with any of the oxadiazole derivatives of the present invention is excellent, the oxadiazole derivative of the present invention is optimal for use as a host material of a light-emitting layer in a light-emitting element. Consequently, another structure of the present invention is a light-emitting element that has a light-emitting layer that contains the aforementioned oxadiazole derivative and a luminescent material.

In particular, because the oxadiazole derivative of the present invention has the characteristic of having a high triplet excitation energy, it is preferable that a phosphorescent compound be used for the luminescent material. By use of this kind of structure, a light-emitting element that has superior luminous efficacy and reliability can be obtained.

Furthermore, a light-emitting element in which a layer that contains the oxadiazole derivative of the present invention is provided in contact with the light-emitting layer is another aspect of the present invention. Because the oxadiazole derivative of the present invention has a high excitation energy, by use of this kind of structure, the diffusion of excitons generated in the light-emitting layer to other layers can be prevented. As a result, a light-emitting element with a high luminous efficacy can be obtained.

Moreover, because the light-emitting element of the present invention that is obtained in this way has the characteristics of having high luminous efficacy and high reliability, low power consumption can be achieved in a light-emitting device (an image display device) in which the light-emitting element is used. Thusly, the present invention also includes light-emitting devices in which the light-emitting elements of the present invention are used. In addition, the present invention also includes electronic devices in which the light-emitting devices are used, as well.

It is to be noted that the "light-emitting device" in the present specification includes image display devices in which the light-emitting elements are used. Moreover, modules in which a connector, for example, an anisotropic film, a tape automated bonding tape (TAB tape), or a tape carrier package (TCP), is attached to a light-emitting device; modules in which the edge of a TAB tape or a TCP is attached to a printed circuit board; and modules in which integrated circuits (ICs) are directly mounted into light-emitting elements by a chip on glass (COG) method shall all be included as light-emitting devices. Furthermore, light-emitting devices that are used in lighting equipment and the like shall also be included.

By implementation of the present invention, a material with a high excitation energy, in particular, a material with a high triplet excitation energy, can be obtained. In addition, compounds that have low crystallinity can be easily synthesized.

Moreover, by application of this kind of material in a light-emitting element, a light-emitting element that has a high luminous efficacy can be provided. Additionally, a light-emitting element with high reliability can be provided.

Furthermore, by fabrication of light-emitting devices in which the aforementioned light-emitting elements are used, light-emitting devices that have high reliability and low power consumption can be provided. Moreover, by application of these light-emitting devices to electronic devices, electronic devices that have high reliability and low power consumption can be provided.

DETAILED DESCRIPTION OF THE INVENTION

Figure 1:
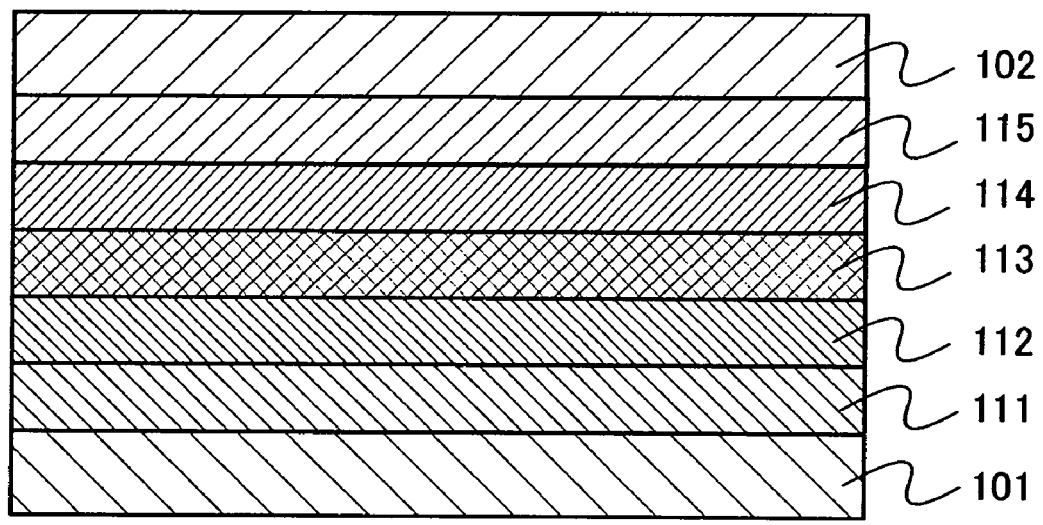
FIG. 1 is a diagram used to describe the element structure of a light-emitting element that contains the oxadiazole derivative of the present invention.

Embodiment Modes of the present invention will be explained below in detail with reference to the accompanying drawings. However, it is to be easily understood that the present invention is not to be considered as being limited to the explanation given below, and various changes and modifications will be apparent to those skilled in the art without any departure from the spirit and scope of the present invention. Therefore, it is to be understood that the present invention is not limited to the defined content of the embodiment modes given below.

Embodiment Mode 1

In the present Embodiment Mode 1, an oxadiazole derivative of the present invention will be described. The oxadiazole derivative of the present invention is represented by the General Formula (G1), that is, (G1-1) or (G1-2), which are given below.

[Chemical Formulas 4: General Formulas (G1), (G1-1), and (G1-2)]

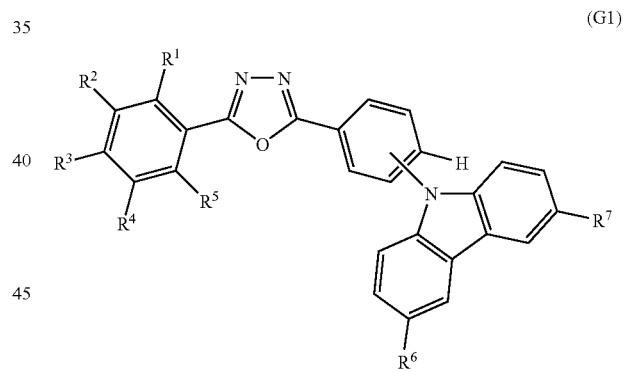

(G1)

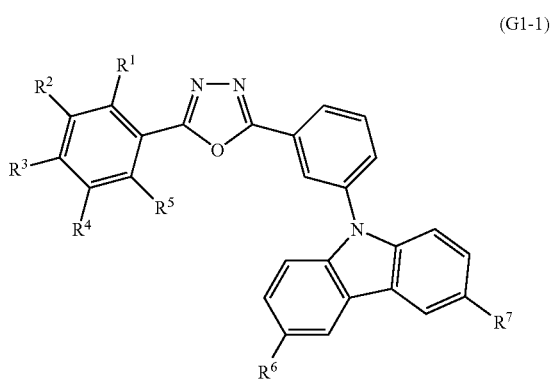

(G1-1)

-continued

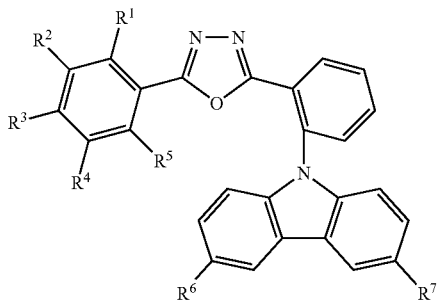
(G1-2)

($R^1$ to $R^7$ each represent either hydrogen or an alkyl group with from 1 to 4 carbon atoms.)

The oxadiazole derivative represented by the General Formula (G1) given above is obtained by coupling, using a metal catalyst, of a halogenated oxadiazole derivative that is represented by General Formula (OXD1) that is given below and a carbazole derivative represented by General Formula (Cz1) that is given below. In addition, hereinafter, first, a synthesis method of the (OXD1) given below will be disclosed.

[Chemical Formula 5: General Formula (OXD1)]

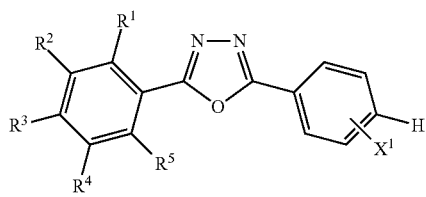
(OXD1)

(In the formula, $R^1$ to $R^5$ each represent either hydrogen or an alkyl group with from 1 to 4 carbon atoms. In addition, $X^1$ represents a halogen group, preferably, a bromo group or an iodine group.)

[Chemical Formula 6: General Formula (Cz1)]

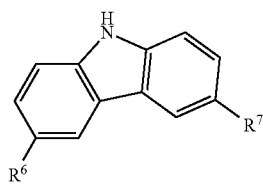
(Cz1)

(In the formula, $R^6$ and $R^7$ each represent either hydrogen or an alkyl group with from 1 to 4 carbon atoms.)

<<a. Synthesis Method of the Halogenated Oxadiazole Derivative (OXD1)>>

The halogenated oxadiazole derivative represented by the General Formula (OXD1) given above can be synthesized as shown in Synthesis Scheme (a) that is given below. That is, first, an ester of aryl halide carboxylic acid (A) and hydrazine are reacted together to synthesize aryl halide hydrazine (B). Next, the aryl halide hydrazine (B) and aryl carboxylic acid halide (C) are reacted together, and a diacyl hydrazine derivative (D) is obtained. Furthermore, the halogenated oxadiazole derivative (OXD1) can be obtained by ring closure by dehydration of the diacyl hydrazine derivative (D) using a dehydrating agent so that a 1,3,4-oxadiazole ring is formed. It is to be noted that, in the Synthesis Scheme (a) given below, $R^1$ to $R^5$ each represent either hydrogen or an alkyl group with from 1 to 4 carbon atoms. In addition, $X^1$ and $X^2$ each represent a halogen group, preferably, a bromo group or an iodine group.

[Chemical Formula 7: Synthesis Scheme (a)]

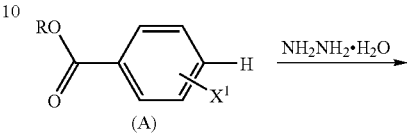
(A)

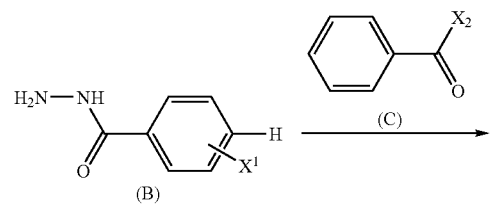
(B)

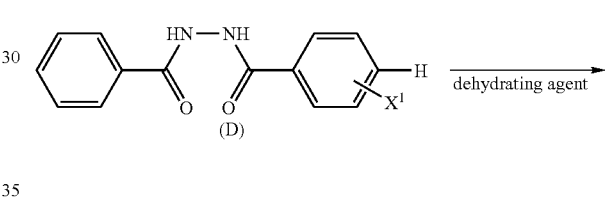
(D)

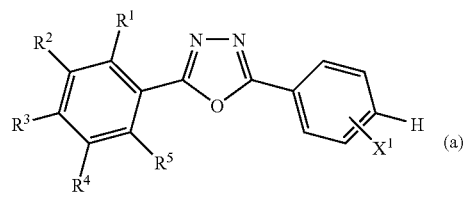
(OXD1)

(a)

In addition, for the dehydrating agent, phosphorus oxychloride, thionyl chloride, or the like can be used.

In addition, the technique used to synthesize the halogenized oxadiazole derivative (OXD1) is not to be limited to that of the Synthesis Scheme (a), and other publicly known techniques can be used.

<<b. Synthesis Method of the Oxadiazole Derivative of the Present Invention Represented by the General Formula (G1)>>

By coupling of the halogenated oxadiazole derivative (OXD1) obtained by the Synthesis Scheme (a) given above and a carbazole derivative (Cz1) using a metal catalyst in the presence of a base, the oxadiazole derivative of the present invention that is represented by the General Formula (G1) is obtained. The synthesis scheme is shown in Synthesis Scheme (b) given below. It is to be noted that, in the Synthesis Scheme (b) given below, $R^1$ to $R^7$ each represent either hydrogen or an alkyl group with from 1 to 4 carbon atoms. In addition, $X^1$ represents a halogen group, preferably, a bromo group or an iodine group.

[Chemical Formula 8: Synthesis Scheme (b)]

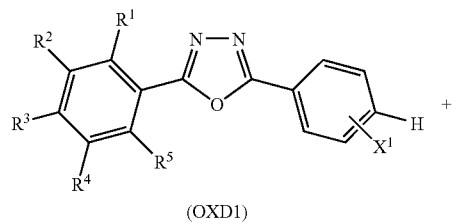

(OXD1)

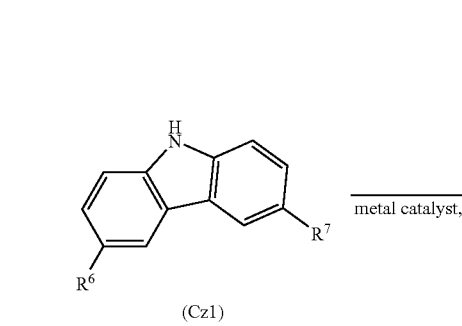

(Cz1)

→ metal catalyst, base

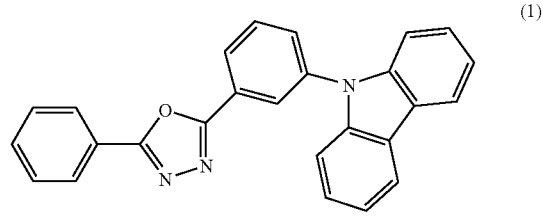

(G1) (b)

It is to be noted that, for the base, an inorganic base such as potassium carbonate, sodium carbonate, or the like or an organic base typified by a metal alkoxide such as sodium tert-butoxide or the like can be used. In addition, for the metal catalyst, a palladium catalyst, monovalent copper, or the like can be given; specifically, palladium acetate, palladium chloride, bis(dibenzylideneacetone)palladium(0), copper(I) iodide, and the like can be given.

It is to be noted that the product of the coupling of (OXD1) and (Cz1) corresponds to the oxadiazole derivative of the General Formula (G1) given above.

<<Specific Structural Formula of the Oxadiazole Derivative of the Present Invention that is Represented by the General Formula (G1)>>

Next, using the General Formula (G1) that is given below, a specific structure of the oxadiazole derivative of the present invention will be described.

[Chemical Formulas 9: General Formulas (G1), (G1-1), and (G1-2)]

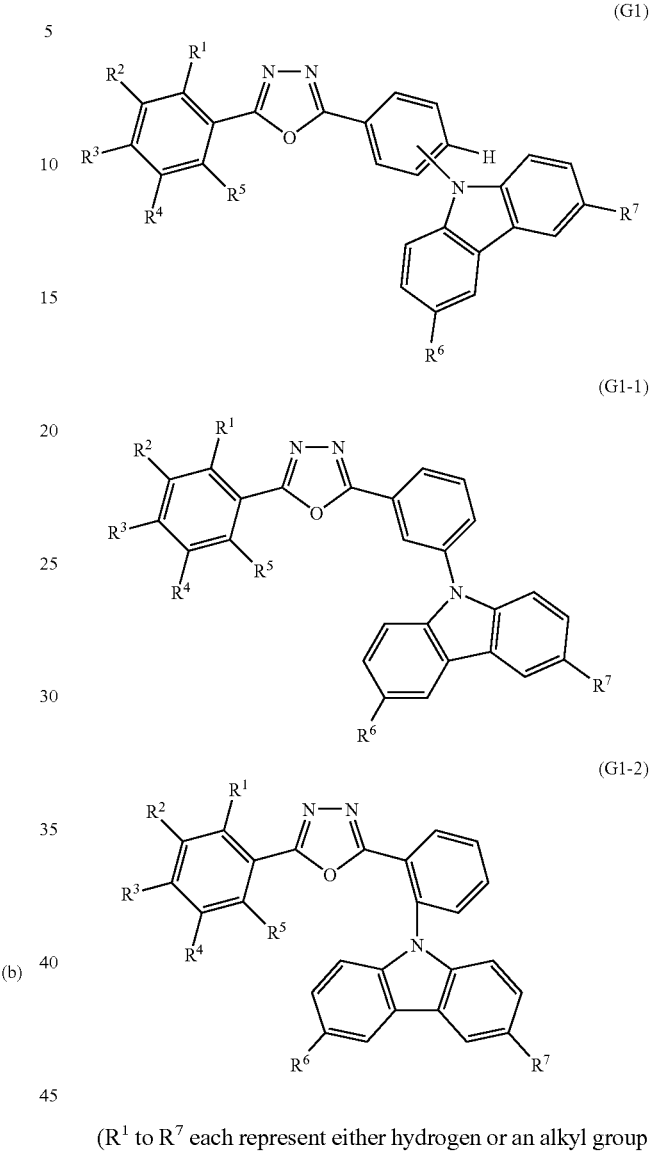

($R^1$ to $R^7$ each represent either hydrogen or an alkyl group with from 1 to 4 carbon atoms.)

For the structure in the General Formula (G1), specific structural formulas of the oxadiazole derivative of the present invention will be listed (Structural Formulas (1) through (22), which are given below). However, the present invention is not to be taken as being limited to these structural formulas.

[Chemical Formulas 10: Structural Formulas (1) through (12)]

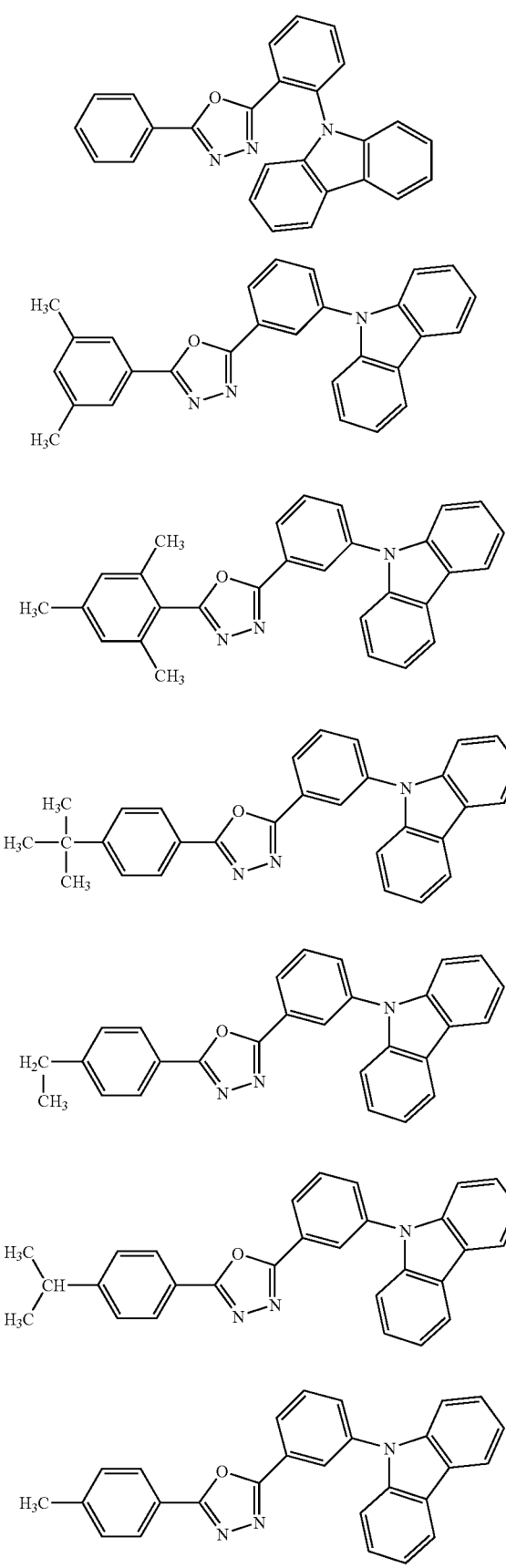
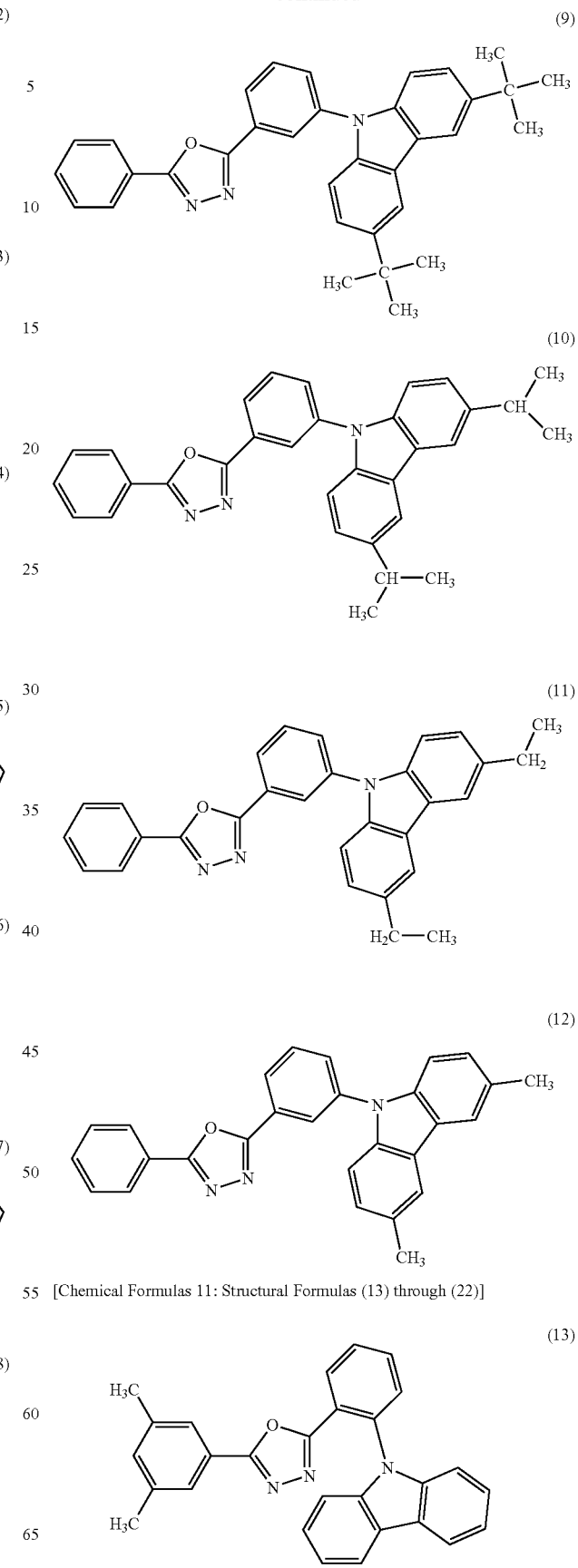
[Chemical Formulas 11: Structural Formulas (13) through (22)]

(14)
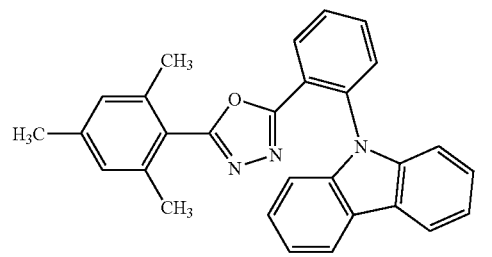

(15)
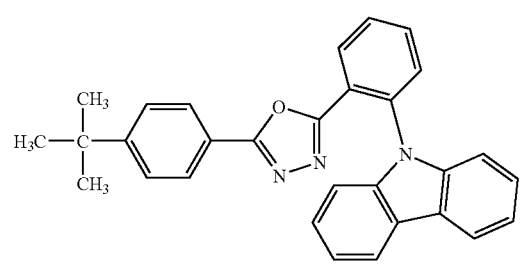

(16)
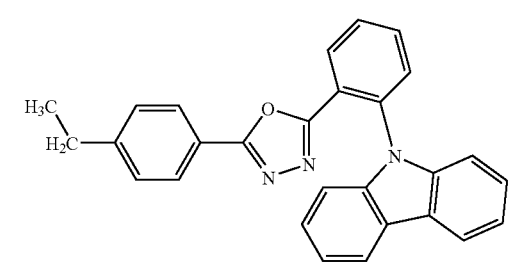

(17)
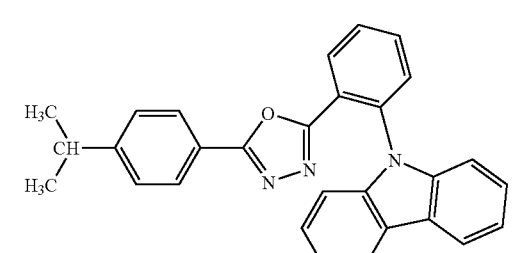

(18)
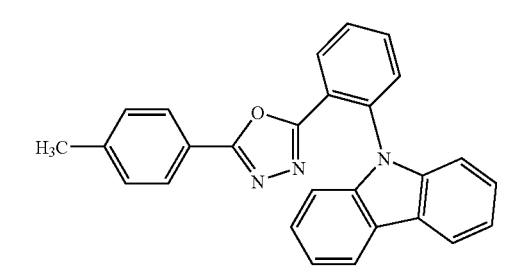

(19)
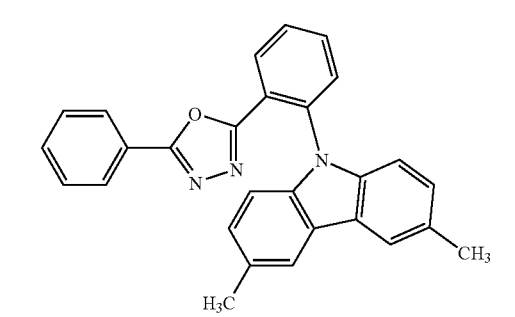

(20)
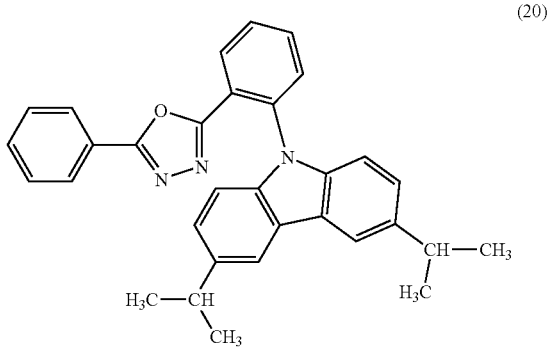

(21)
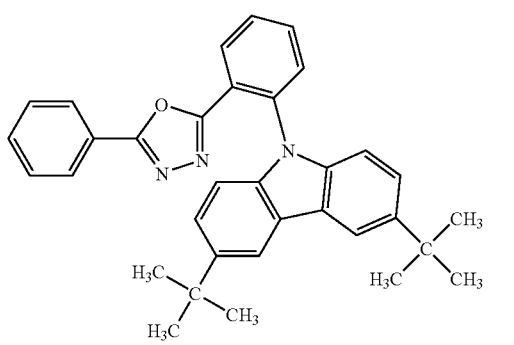

(22)
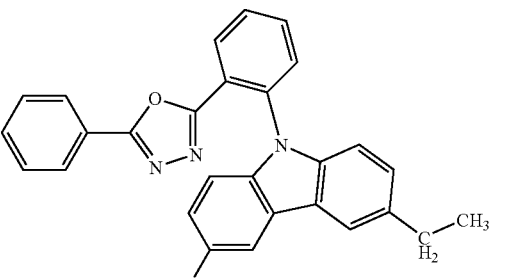

Embodiment Mode 2

In the present Embodiment Mode 2, a mode of a light-emitting element in which the oxadiazole derivative of the present invention that is described in Embodiment Mode 1 is used as a host material of a light-emitting layer will be described using FIG. 1.

FIG. 1 shows a light-emitting element having a light-emitting layer 113 interposed between a first electrode 101 and a second electrode 102. The light-emitting layer 113 contains the oxadiazole derivative of the present invention and a light-emitting material. In the present Embodiment Mode 2, the oxadiazole derivative of the present invention is a host material in the light-emitting layer 113 and the light-emitting material is a guest material in the light-emitting layer 113.

By application of voltage to this kind of light-emitting element, holes injected from the first electrode 101 side and electrons injected from the second electrode 102 side recombine in the light-emitting layer 113, and the light-emitting material is placed in an excited state. The light-emitting material in the excited state emits light whenever the excited material returns to the ground state. Because the excitation energy of the oxadiazole derivative of the present invention is high, there is no quenching of the light-emitting material that has been placed in the excited state, which can lead to emission of light at high efficiency. It is to be noted that, in the light-emitting element of the present Embodiment Mode 2, the first electrode 101 functions as an anode and the second electrode 102 functions as a cathode.

There are no particular limitations on the material used for the light-emitting material (that is, on the guest material); however, because the oxadiazole derivative of the present invention has a high triplet excitation energy, it is preferable that the guest material be a phosphorescent compound. Specifically, bis[2-(4',6'-difluorophenyl)pyridinato-N,$C^{2'}$]iridium(III) picolinate (abbreviated designation: FIrpic); tris(2-phenylpyridinato-N,$C^{2'}$)iridium(III) (abbreviated designation: Ir(ppy)$_3$); bis(2-phenylpyridinato-N,$C^{2'}$)iridium (III) acetylacetonate (abbreviated designation: Ir(ppy)$_2$(acac)); bis(2-phenylbenzothiazolato-N,$C^{2'}$)iridium(III) acetylacetonate (abbreviated designation: Ir(bt)$_2$(acac)); tris (2-phenylquinolinato-N,$C^{2'}$)iridium(III) (abbreviated designation: Ir(pq)$_3$); bis(2-phenylquinolinato-N,$C^{2'}$)iridium(III) acetylacetonate (abbreviated designation: Ir(pq)$_2$(acac)); bis [2-(2'-benzo[4,5-α]thienyl)pyridinato-N,$C^{2'}$)iridium(III) acetylacetonate (abbreviated designation: Ir(btp)$_2$(acac)); bis (1-phenylisoquinolinato-N,$C^{2'}$)iridium(III) acetylacetonate (abbreviated designation: Ir(piq)$_2$(acac)); (acetylacetonato) bis[2,3-bis(4-fluorophenyl)quinoxalinato]iridium(III) (abbreviated designation: Ir(Fdpq)$_2$(acac)); 2,3,7,8,12,13,17,18-octaethyl-21H,23H-porphyrin platinum(II) (abbreviated designation: PtOEP); and the like can be given.

Alternatively, for the light-emitting material, a fluorescent compound can also be used; specifically, perylene; 2,5,8,11-tetra(tert-butyl)perylene (abbreviated designation: TBP); 4,4'-bis[2-(N-ethylcarbazol-3-yl)vinyl]biphenyl (abbreviated designation: BCzVBi); 5,12-diphenyltetracene; N,N'-dimethylquinacridone (abbreviated designation: DMQd); N,N'-diphenylquinacridone (abbreviated designation: DPQd); 4-dicyanomethylene-2-isopropyl-6-[2-(1,1,7,7-tetramethyljulolidine-9-yl)ethenyl]-4H-pyran (abbreviated designation: DCJTI); rubrene; coumarin 6; coumarin 30; and the like can be given.

There are no particular limitations on the material used for the first electrode 101; however, it is preferable that the first electrode 101 be formed of a material that has a high work function when the first electrode 101 functions as an anode as in the present Embodiment Mode 2. Specifically, in addition to indium tin oxide (ITO), indium tin oxide that contains silicon oxide (ITSO), or indium oxide that contains zinc oxide at a weight percent of from 2 wt % to 20 wt % (IZO), gold (Au), platinum (Pt), nickel (Ni), tungsten (W), chromium (Cr), molybdenum (Mo), iron (Fe), cobalt (Co), copper (Cu), palladium (Pd), or the like can be used. It is to be noted that the first electrode 101 can be formed using, for example, a sputtering method, an evaporation method, or the like.

There are no particular limitations on the material used for the second electrode 102; however, it is preferable that the second electrode 102 be formed of a material that has a low work function when the second electrode 102 functions as a cathode as in the present Embodiment Mode 2. Specifically, in addition to aluminum (Al) or indium (In), an alkali metal such as lithium (Li), cesium (Cs), or the like; an alkali earth metal such as magnesium (Mg), calcium (Ca), or the like; or a rare earth metal such as erbium (Er), ytterbium (Yb), or the like can be used. Furthermore, an alloy like an aluminum-lithium (AlLi) alloy or a magnesium-silver (MgAg) alloy can also be used. It is to be noted that the second electrode 102 can be formed using, for example, a sputtering method, an evaporation method, or the like.

It is to be noted that, in order that emitted light be extracted out to external, it is preferable that either one of or both the first electrode 101 and the second electrode 102 be an electrode that is formed of a conductive film of ITO or the like that transmits visible light or an electrode that is formed at a thickness of from several nanometers to several tens of nanometers in order to be able to transmit visible light.

In addition, a hole-transporting layer 112 may be provided between the first electrode 101 and the light-emitting layer 113 as shown in FIG. 1. Here, the hole-transporting layer is a layer that has a function used to transport holes injected from the first electrode 101 into the light-emitting layer 113. In this way, by provision of the hole-transporting layer 112 and by isolation of the first electrode 101 and the light-emitting layer 113 from each other, quenching of light emission due to metal can be prevented. However, the hole-transporting layer 112 is not absolutely necessary.

There are no particular limitations on the material used for the hole-transporting layer 112; typically, an aromatic amine compound such as 4,4'-bis[N-(1-naphthyl)-N-phenylamino] biphenyl (abbreviated designation: NPB); 4,4'-bis[N-(3-methylphenyl)-N-phenylamino]biphenyl (abbreviated designation: TPD); 4,4'-bis[N-(9,9-dimethylfluorene-2-yl)-N-phenylamino]biphenyl (abbreviated designation: DFLDPBi); 4,4',4''-tris(N,N-diphenylamino)triphenylamine (abbreviated designation: TDATA); 4,4',4'-tris[N-(3-methylphenyl)-N-phenylamino]triphenylamine (abbreviated designation: m-MTDATA); or the like can be used. In addition, a macromolecular compound such as poly(4-vinyltriphenylamine) (abbreviated designation: PVTPA) or the like can also be used.

It is to be noted that the hole-transporting layer 112 may have a multilayer structure formed of two or more layers stacked together. Furthermore, the hole-transporting layer 112 may be formed of two or more types of materials that are mixed together.

Moreover, an electron-transporting layer 114 may be provided between the second electrode 102 and the light-emitting layer 113 as shown in FIG. 1. Here, the electron-transporting layer is a layer that has a function used to transport electrons injected from the second electrode 102 into the light-emitting layer 113. In this way, by provision of the electron-transporting layer 114 and by isolation of the second electrode 102 and the light-emitting layer 113 from each other, quenching of light emission that is attributable to metals can be prevented. However, the electron-transporting layer 114 is not absolutely necessary.

There are no particular limitations on the material used for the electron-transporting layer 114; typically, a metal complex such as tris(8-quinolinolato)aluminum (abbreviated designation: Alq$_3$); tris(4-methyl-8-quinolinolato)aluminum (abbreviated designation: Almq$_3$); bis(10-hydroxybenzo[h] quinolinato)beryllium (abbreviated designation: BeBq$_2$); bis (2-methyl-8-quinolinolato)(4-phenylphenolato)aluminum (abbreviated designation: BAlq); bis[2-(2'-hydroxyphenyl) benzoxazolato]zinc (abbreviated designation: Zn(BOX)$_2$); bis[2-(2'-hydroxyphenyl)benzothiazolato]zinc (abbreviated designation: Zn(BTZ)$_2$); and the like can be given. Moreover, a heteroaromatic compound such as 2-(4-biphenylyl)-5-(4-tert-butylphenyl)-1,3,4-oxadiazole (abbreviated designation: PBD); 1,3-bis[5-(p-tert-butylphenyl)-1,3,4-oxadiazol-2-yl] benzene (abbreviated designation: OXD-7); 3-(4-tert-biphenylyl)-4-phenyl-5-(4-butylphenyl)-1,2,4-triazole (abbreviated designation: TAZ); 3-(4-tert-butylphenyl)-4-(4-ethylphenyl)-5-(4-biphenylyl)-1,2,4-triazole (abbreviated designation: p-EtTAZ); bathophenanthroline (abbreviated designation: BPhen); bathocuproine (abbreviated designation: BCP); 4-4'-bis(5-methylbenzoxazol-2-yl)stilbene abbreviated designation: BzOs); or the like can be used, as well. In addition, a macromolecular compound such as poly(2,5-pyridine-diyl) (abbreviated designation: PPy) or the like can also be used.

It is to be noted that the electron-transporting layer 114 may have a multilayer structure formed of two or more layers stacked together. Furthermore, the electron-transporting layer 114 may be formed of two or more types of materials that are mixed together.

Furthermore, a hole-injection layer 111 may be provided between the first electrode 101 and the hole-transporting layer 112 as shown in FIG. 1. Here, the hole-injection layer is a layer that has a function used to assist in the injection of holes into the hole-transporting layer 112 from the electrode that is used to function as an anode. However, the hole-injection layer 111 is not absolutely necessary.

There are no particular limitations on the material used for the hole-injection layer 111; a metal oxide such as an oxide of vanadium, an oxide of niobium, an oxide of tantalum, an oxide of chromium, an oxide of molybdenum, an oxide of tungsten, an oxide of manganese, an oxide of rhenium, an oxide of ruthenium, or the like can be used. In addition, a phthalocyanine compound such as phthalocyanine (abbreviated designation: $H_2PC$), copper phthalocyanine (abbreviated designation: CuPc), or the like can also be used. Moreover, any of the materials given above that are used to form the hole-transporting layer 112 can be used, as well. Additionally, a macromolecular compound such as a mixture of poly(ethylenedioxythiophene) and poly(styrenesulfonate) (abbreviated designation: PEDOT:PSS) can also be used.

Alternatively, for the hole-injection layer 111, a composite material formed of a mixture of an organic compound and an electron acceptor may be used. Because holes are generated in the organic compound by the electron acceptor, this kind of composite material has superior hole-injection and hole-transporting properties. In this case, for the organic compound, it is preferable that it be a material that excels in the transportation of generated holes; specifically, any of the materials (the aromatic amine compounds and the like) given above that are used to form the hole-transporting layer 112 can be used, for example. The electron acceptor should be a material that exhibits an electron-accepting property with respect to the organic compound. Specifically, it is preferable that the material used for the electron acceptor be an oxide of a transition metal; for example, an oxide of vanadium, an oxide of niobium, an oxide of tantalum, an oxide of chromium, an oxide of molybdenum, an oxide of tungsten, an oxide of manganese, an oxide of rhenium, an oxide of ruthenium, and the like can be given. Furthermore, a Lewis acid like iron(III) chloride, aluminum(III) chloride, or the like can be used, as well. Alternatively, an organic compound such as 7,7,8,8-tetracyano-2,3,5,6-tetrafluoroquinodimethane (abbreviated designation: F4-TCNQ) or the like can be used, as well.

It is to be noted that the hole-injection layer 111 may have a multilayer structure formed of two or more layers stacked together. Furthermore, the hole-injection layer 111 may be formed of two or more types of materials that are mixed together.

Furthermore, an electron-injection layer 115 may be provided between the second electrode 102 and the electron-transporting layer 114 as shown in FIG. 1. Here, the electron-injection layer is a layer that has a function used to assist in the injection of electrons into the electron-transporting layer 114 from the electrode that is used to function as a cathode. However, the electron-injection layer 115 is not absolutely necessary.

There are no particular limitations on the material used for the electron-injection layer 115; an alkali metal compound or alkali earth metal compound like lithium fluoride (LiF), cesium fluoride (CsF), calcium fluoride ($CaF_2$), or lithium oxide ($LiO_x$) can be used. Alternatively, a rare earth metal compound like erbium fluoride ($ErF_3$) can be used. Moreover, any of the materials given above that are used to form the electron-transporting layer 114 can be used, as well.

Alternatively, for the electron-injection layer 115, a composite material formed of a mixture of an organic compound and an electron donator may be used. Because electrons are generated in the organic compound by the electron donator, this kind of composite material has superior electron-injection and electron-transporting properties. In this case, for the organic compound, it is preferable that it be a material that excels in the transportation of generated electrons; specifically, any of the materials (the metal complexes, the heteroaromatic compounds, and the like) given above that are used to form the electron-transporting layer 114 can be used, for example. The electron donator should be a material that exhibits an electron-donating property with respect to the organic compound. Specifically, it is preferable that the material used for the electron acceptor be an alkali metal, an alkali earth metal, or a rare earth metal, and lithium, cesium, magnesium, calcium, erbium, ytterbium, and the like can be given as examples thereof. Specifically, it is preferable that the material be an alkali metal compound or an alkali earth metal compound, and lithium oxide ($LiO_x$), calcium oxide ($CaO_x$), barium oxide ($BaO_x$), cesium carbonate ($Cs_2O_3$), and the like can be given as examples thereof. Furthermore, a Lewis base like magnesium oxide or the like can be used, as well. Alternatively, an organic compound such as tetrathiafulvalene (abbreviated designation: TTF) or the like can be used, as well.

In the light-emitting element of the present invention that is described above, the hole-injection layer 111, the hole-transporting layer 112, the light-emitting layer 113, the electron-transporting layer 114, and the electron-injection layer 115 may each be formed using any of an evaporation method, an inkjet printing method, a coating method, or the like. Furthermore, the first electrode 101 and the second electrode 102 may each be formed using any of a sputtering method, an evaporation method, an inkjet printing method, a coating method, or the like.

Embodiment Mode 3

In the present Embodiment Mode 3, a mode of a light-emitting element in which the oxadiazole derivative of the present invention is used as an exciton blocking layer will be described using FIG. 2 and FIG. 3. It is to be noted that an exciton blocking layer is one kind of a hole-transporting layer or electron-transporting layer that is provided in contact with a light-emitting layer and, in particular, is a layer that has a higher excitation energy than the light-emitting layer and that has a function used to block excitons in the light-emitting layer from moving into other layers.

Figure 2:
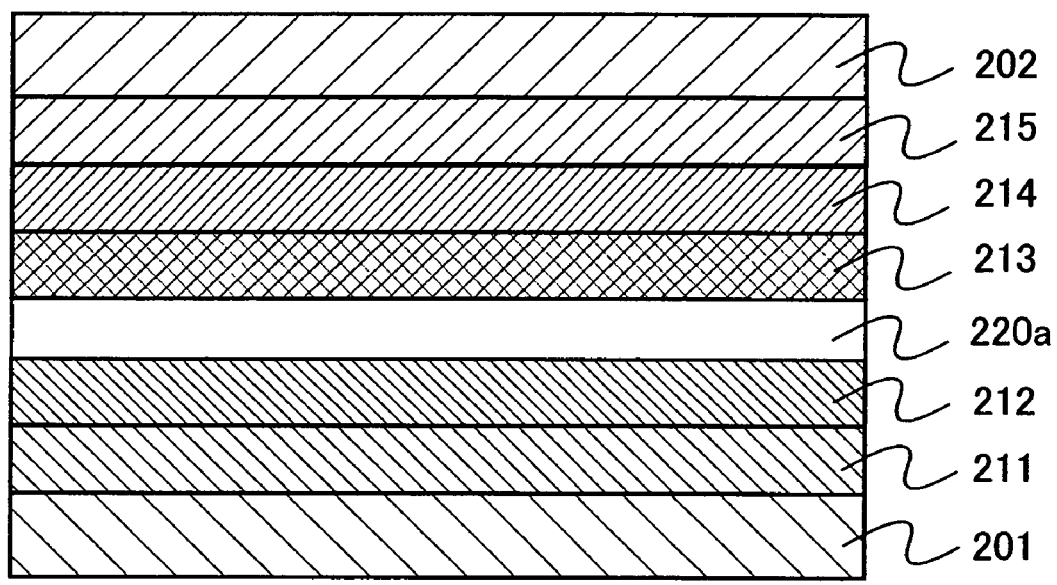
FIG. 2 is a diagram used to describe the element structure of a light-emitting element that contains the oxadiazole derivative of the present invention.

In the light-emitting element shown in FIG. 2, a light-emitting layer 213 is provided between a first electrode 201 that functions as an anode and a second electrode 202 that functions as a cathode. An exciton blocking layer 220a that is made from the oxadiazole derivative of the present invention is provided in contact with the anode side of the light-emitting layer 213. Consequently, for the light-emitting element of FIG. 2, the exciton blocking layer 220a is a kind of hole-transporting layer.

Figure 3:
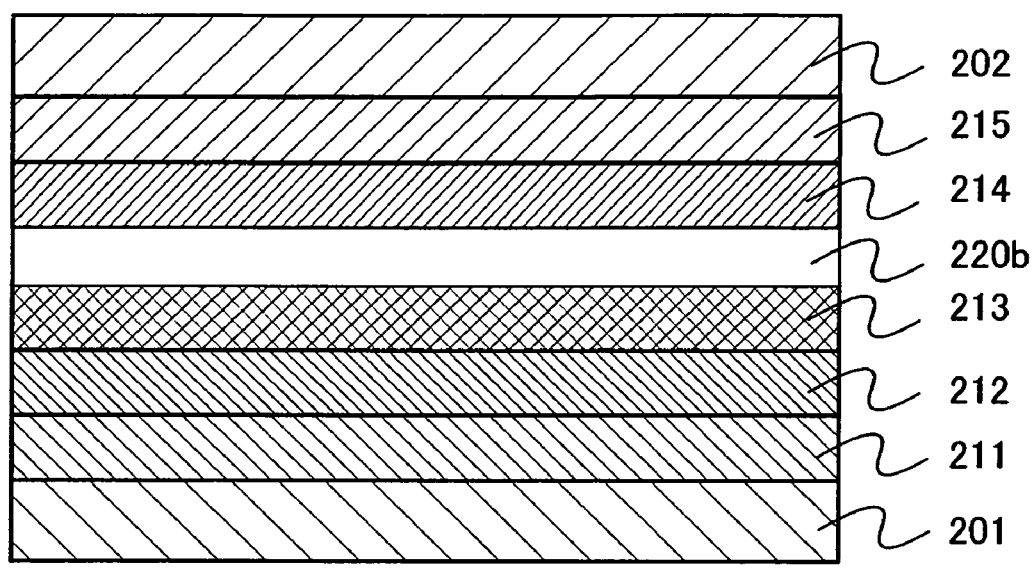
FIG. 3 is a diagram used to describe the element structure of a light-emitting element that contains the oxadiazole derivative of the present invention.

In addition, in the light-emitting element shown in FIG. 3, a light-emitting layer 213 is provided between a first electrode 201 that functions as an anode and a second electrode 202 that functions as a cathode. An exciton blocking layer 220b that is made from the oxadiazole derivative of the present invention is provided in contact with the cathode side of the light-emitting layer 213. Consequently, for the light-emitting element of FIG. 3, the exciton blocking layer 220b is a kind of electron-transporting layer.

By the light-emitting element being set to have a structure like the one shown in FIG. 2 or FIG. 3, excitons generated in the light-emitting layer 213 can be efficiently trapped within the light-emitting layer 213. Furthermore, because the oxadiazole derivative of the present invention is bipolar, it has the characteristic of being able to be used as an exciton blocking layer on either the anode side or the cathode side of light-emitting layer, as shown in FIG. 2 and FIG. 3. Consequently, although not shown in either FIG. 2 or FIG. 3, an exciton blocking layer that is made from the oxadiazole derivative of the present invention can be provided on both sides of the light-emitting layer 213.

Here, a variety of structures can be applied for the light-emitting layer 213. For example, the light-emitting layer 213 made from a host material and a guest material is formed, as one example. For specific examples of the host material used in this case, in addition to NPB, DFLDPBi, $ALq_3$, BAlq, and the like, 4,4'-di(N-carbazolyl)biphenyl (abbreviated designation: CBP), 2-tert-butyl-9,10-di(2-naphthyl)anthracene (abbreviated designation: t-BuDNA), 9-[4-(9-carbazolyl)phenyl]-10-phenylanthracene (abbreviated designation: CzPA), and the like can be given. Furthermore, for specific examples of the guest material used in this case, in addition to the phosphorescent compounds and fluorescent compounds described in the preceding Embodiment Mode 2, 9-(4-{N-[4-(carbazol-9-yl)phenyl]-N-phenylamino}phenyl)-10-phenylanthracene (abbreviated designation: YGAPA), and the like can be given.

It is to be noted that, the first electrode 201 may be set to have the same structure as the first electrode 101 described in the preceding Embodiment Mode 2. In addition, the second electrode 202 may also be set to have the same structure as the second electrode 102 described in the preceding Embodiment Mode 2.

Moreover, a hole-injection layer 211, a hole-transporting layer 212, an electron-transporting layer 214, and an electron-injection layer 215 are provided as shown in FIG. 2 and FIG. 3; the structure of each of the respective layers described in the preceding Embodiment Mode 2 may be applied for the structure of each of these layers, as well. However, these layers are not absolutely necessary and may be formed as appropriate based on the characteristics of the element.

Embodiment Mode 4

Figure 4A:
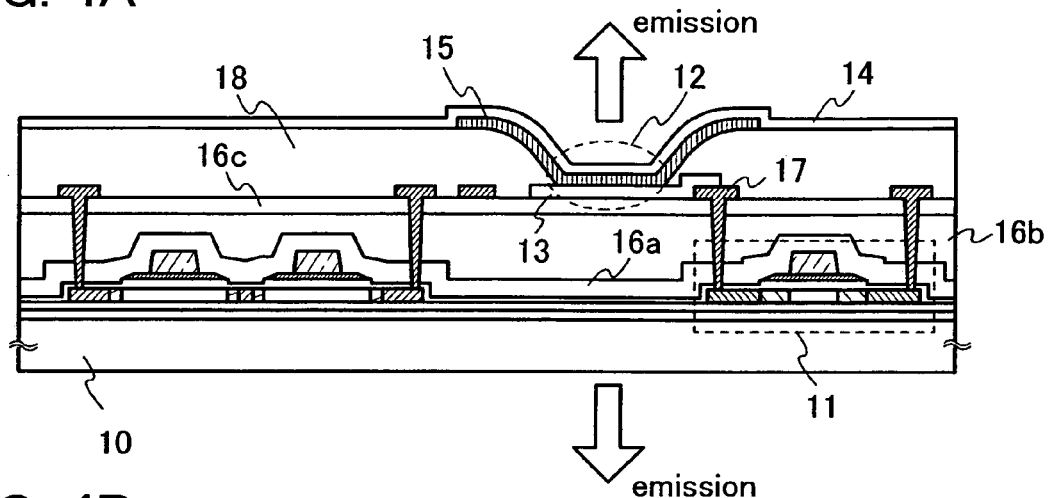
FIGS. 4A to 4C are diagrams used in the description of light-emitting devices in which the light-emitting elements of the present invention are used.
Figure 4B:
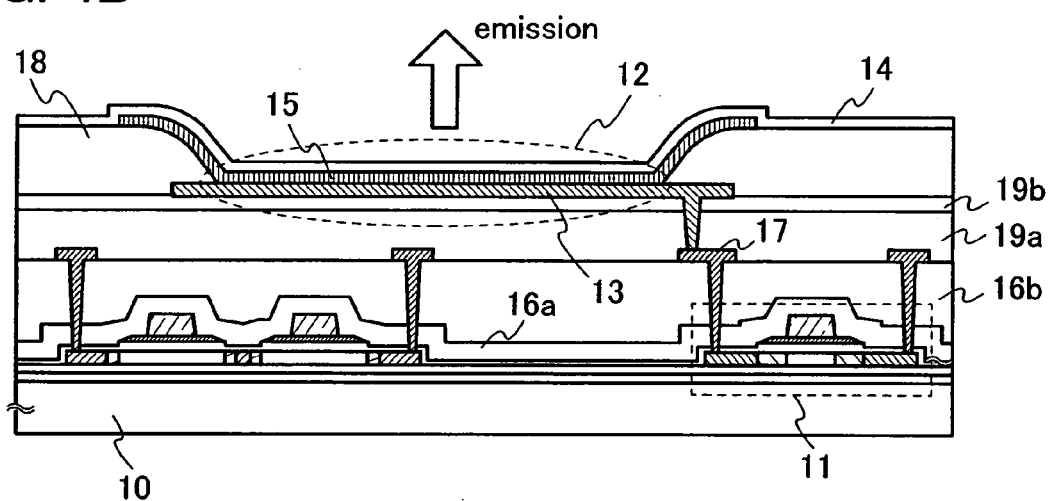
Figure 4C:
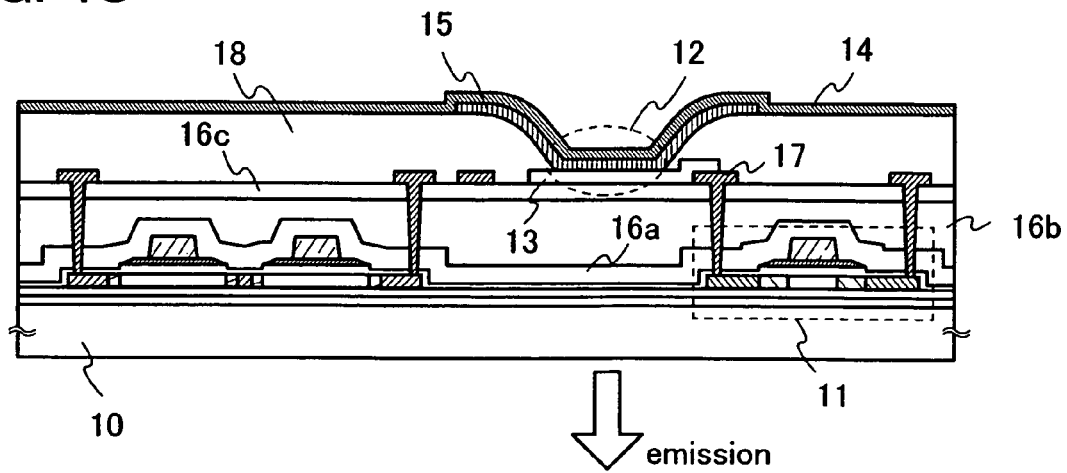

In the present Embodiment Mode 4, modes of a light-emitting device in which the light-emitting element of the present invention is included will be described using FIGS. 4A to 4C. FIGS. 4A to 4C are cross-sectional-view diagrams of different modes of the light-emitting device.

In FIGS. 4A to 4C, enclosed by dotted lines formed into a rectangle is a transistor 11 that is provided in order to drive a light-emitting element 12 of the present invention. The light-emitting element 12 is a light-emitting element of the present invention that has a layer 15 that includes a light-emitting layer interposed between a first electrode 13 and a second electrode 14, and the light-emitting element 12 contains the oxadiazole derivative of the present invention. Specifically, the light-emitting element 12 has a structure like that described in Embodiment Mode 2 or Embodiment Mode 3. A drain region of the transistor 11 and the first electrode 13 are electrically connected to each other by a wiring 17 that runs through a first interlayer insulating film 16 (16a, 16b, and 16c). Moreover, the light-emitting element 12 is isolated from other light-emitting elements that are provided adjacent thereto by a partition wall layer 18. The light-emitting device of the present invention that has this kind of structure is provided over a substrate 10 in the present Embodiment Mode 4.

It is to be noted that the transistor 11 shown in FIGS. 4A to 4C is a top-gate transistor in which the gate electrode is formed on the side opposite from the substrate, centered on the semiconductor layer. However, there are no particular limitations on the structure of the transistor 11; for example, the transistor 11 may be a bottom-gate transistor, as well. In addition, when the transistor 11 is a bottom-gate transistor, the transistor may be one in which a protective film is formed over a semiconductor layer used to form the channel (a channel-protected transistor) or one in which part of the semiconductor layer used to form the channel is formed into a concave-shape (a channel-etched transistor).

Furthermore, the semiconductor layer used to form the transistor 11 may be either a crystalline semiconductor layer or an amorphous semiconductor layer. Moreover, the semiconductor layer may be semi-amorphous or the like, as well.

It is to be noted that a semi-amorphous semiconductor can be described as follows. A semi-amorphous semiconductor is a semiconductor that has a structure that is somewhere between an amorphous structure and a crystalline structure (which includes single crystal and polycrystalline structures) and that has a third state that is stable in terms of free energy and includes a crystalline region that has short-range order and lattice strain. Furthermore, crystal grains of from 0.5 nm to 20 nm are contained in a region of at least one part of a semi-amorphous semiconductor film. Raman spectra derived using LO phonons are shifted toward wavenumbers lower than 520 $cm^{-1}$. Diffraction peaks for (111) and (220), which originate with the Si crystal lattice, are observed by X-ray diffraction. To terminate dangling bonds, the semi-amorphous semiconductor film contains hydrogen or a halogen at a concentration of at least 1 at. %. So-called semi-amorphous semiconductors are also referred to as microcrystal semiconductors. The semi-amorphous semiconductor is formed by glow discharge decomposition (plasma CVD) of a gas that contains a silicide. For the gas that contains a silicide, in addition to $SiH_4$, $Si_2H_6$, $SiH_2Cl_2$, $SiHCl_3$, $SiCl_4$, $SiF_4$, or the like can be used. This gas that contains a silicide may be diluted with $H_2$ or $H_2$ and one or more noble gas elements selected from He, Ar, Kr, and Ne. The dilution ratio is in the range of from 2 times to 1000 times, the pressure is from about 0.1 Pa to about 133 Pa, and the power supply frequency is from 1 MHz to 120 MHz, preferably, from 13 MHz to 60 MHz. The heating temperature for the substrate is 300° C. or less, preferably, from 100° C. to 250° C. For the impurity element in the film, it is desirable that the concentration of the impurity element of an atmospheric component such as oxygen, nitrogen, carbon, or the like be set to be $1\times10^{20}$ atoms/$cm^3$ or less; in particular, it is desirable that the concentration of oxygen be set to be $5\times10^{19}$ atoms/$cm^3$ or less, preferably, $1\times10^{19}$ atoms/$cm^3$ or less. It is to be noted that the mobility of a thin film transistor (TFT) formed using a semiconductor that is semi-amorphous comes to be from about 1 $cm^2/(V\cdot s)$ to about 10 $cm^2/(V\cdot s)$.

Furthermore, for specific examples for when the semiconductor layer is formed of a crystalline semiconductor, a semiconductor formed from single crystal or polycrystalline silicon, silicon-germanium, and the like can be given. These crystalline semiconductors may be crystallized semiconductors that are formed by laser crystallization, or they may be crystallized semiconductors that are formed by crystallization by a solid-phase growth method using nickel or the like, for example.

It is to be noted that when the semiconductor layer is formed of an amorphous material, for example, amorphous silicon, it is preferable that the transistor 11 and other transistors (transistors that make up a circuit that is used to drive a light-emitting element) of which a circuit provided in the light-emitting device is formed all be formed as n-channel transistors. When the semiconductor layer is formed of a material other than an amorphous material, the light-emitting device may be a light-emitting device that has a circuit that is formed of either n-channel transistors or p-channel transistors or a light-emitting device that has a circuit that is formed of both n-channel transistors and p-channel transistors.

Moreover, the first interlayer insulating layer 16 (16a to 16c) may be multiple layers as shown in FIGS. 4A and 4C or a single layer. It is to be noted that the first interlayer insulating layer 16a is made from an inorganic substance like silicon oxide or silicon nitride. The first interlayer insulating layer 16b is made from a self-planarizing material of acrylic or siloxane (an organic group that contains at least hydrogen as a substituent and whose skeletal structure is made up of bonds of silicon (Si) and oxygen (O)) or silicon oxide that can be applied by coating and formed into films. Furthermore, the first interlayer insulating layer 16c is made of a silicon nitride film that contains argon (Ar). It is to be noted that there are no particular limitations on the materials used for each of the layers of the first interlayer insulating layer 16, and materials other than the ones given here may be used, as well. In addition, layers made from materials other than the ones given here may be combined together to form the first interlayer insulating layer 16, as well. In this way, the first interlayer insulating layer 16 (16a to 16c) may be made from layers that are formed using both inorganic films and organic films, or the first interlayer insulating layer 16 (16a to 16c) may be made from layers that are formed using either inorganic films or organic films.

It is preferable that the shape of the partition wall layer 18 be one in which the radius of curvature continuously changes along the edges. Furthermore, the partition wall layer 18 is formed using acrylic, siloxane, resist, silicon oxide, or the like. It is to be noted that the partition wall layer 18 may be formed using either an inorganic film or an organic film or formed using both an inorganic film and an organic film.

It is to be noted that, in FIGS. 4A and 4C, the structure is one in which only the first interlayer insulating layer 16 (16a to 16c) is provided between the transistor 11 and the light-emitting element 12; however, the structure may be one in which, as shown in FIG. 4B, in addition to the first interlayer insulating layer 16 (16a to 16c), a second interlayer insulating layer 19 (19a and 19b) is also provided between the transistor 11 and the light-emitting element 12. In the light-emitting device shown in FIG. 4B, the first electrode 13 is connected to the wiring 17, which passes through the second interlayer insulating layer 19 (19a and 19b).

As with the first interlayer insulating layer 16, the second interlayer insulating layer 19 may be multiple layers or a single layer. The second interlayer insulating layer 19a is made from a self-planarizing material of acrylic or siloxane (an organic group that contains hydrogen at least as a substituent and whose skeletal structure is made up of bonds of silicon (Si) and oxygen (O)) or silicon oxide that can be applied by coating and formed into films. The second interlayer insulating layer 19b is made from a silicon nitride film that contains argon (Ar). It is to be noted that there are no particular limitations on the materials used for each of the layers of the second interlayer insulating layer 19, and a material other than one of the materials given here may be used, as well. In addition, layers made from materials other than the ones given here may be combined together to form the second interlayer insulating layer 19, as well. In this way, the second interlayer insulating layer 19 may be made from layers that are formed using both inorganic films and organic films, or the second interlayer insulating layer 19 may be made from layers that are formed using either inorganic films or organic films.

In the light-emitting element 12, when either of the first electrode and the second electrode is formed of a material that transmits light, as shown by the white arrows in FIG. 4A, light can be extracted from both the first electrode 13 side and the second electrode 14 side. Furthermore, when only the second electrode 14 is formed of a material that transmits light, as shown by the white arrow in FIG. 4B, light can be extracted from the second electrode 14 side only. In this case, it is preferable that the first electrode 13 be formed of a material that has a high reflectance ratio or that a film (a reflective film) that is made from a material that has a high reflectance ratio be provided below the first electrode 13. In addition, when only the first electrode 13 is formed of a material that transmits light, as shown by the white arrow in FIG. 4C, light can be extracted from the first electrode 13 side only. In this case, it is preferable that the second electrode 14 be formed of a material that has a high reflectance ratio or that a reflective film be provided over the second electrode 14.

Furthermore, the light-emitting element 12 may be an element in which the layer 15 that includes a light-emitting layer is stacked so as to operate when a voltage is applied so that the electric potential of the second electrode 14 comes to be higher than the electric potential of the first electrode 13, or the light-emitting element 12 may be an element in which the layer 15 that includes a light-emitting layer is stacked so as to operate when a voltage is applied so that the electric potential of the second electrode 14 comes to be lower than the electric potential of the first electrode 13. For the former case, the transistor 11 is an n-channel transistor, and for the latter case, the transistor 11 is a p-channel transistor.

Figure 8A:
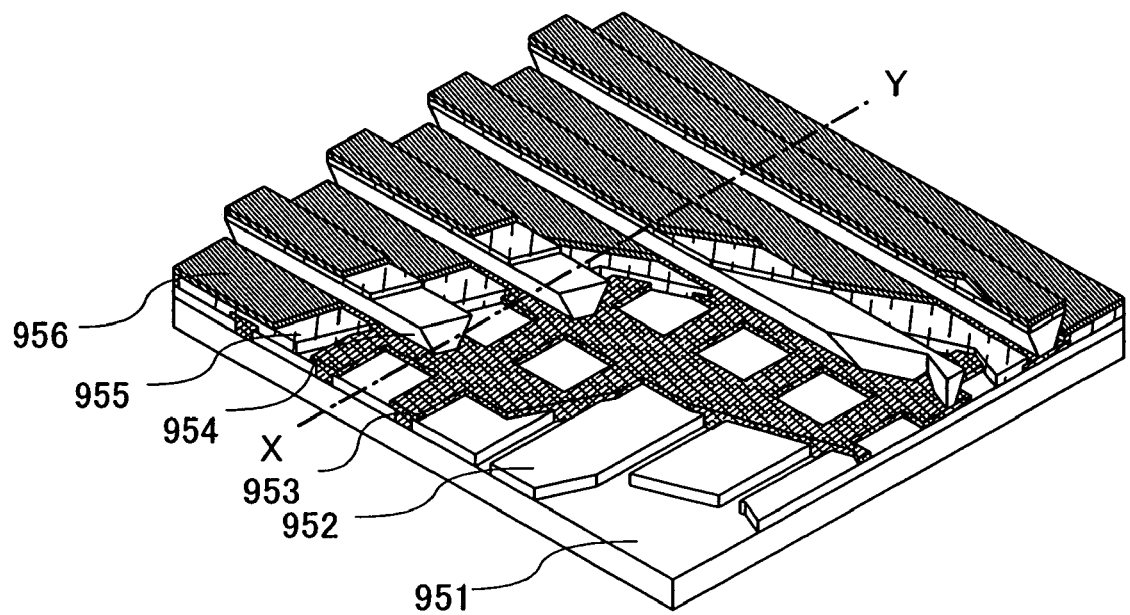
FIGS. 8A and 8B are diagrams used in the description of a light-emitting device in which the light-emitting elements of the present invention are used.
Figure 8B:
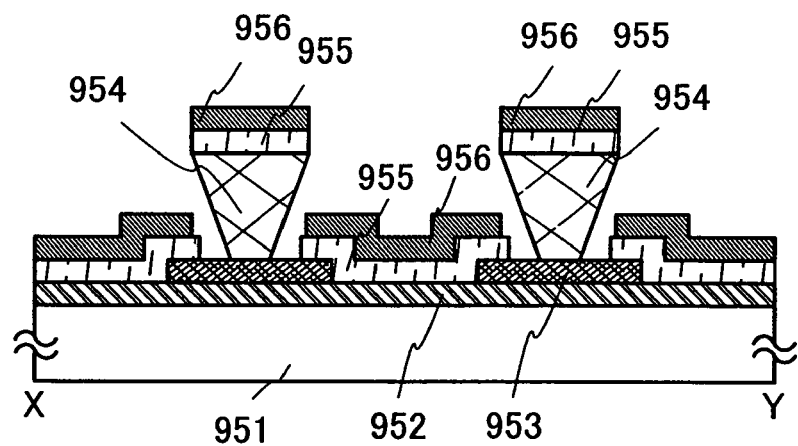

As described above, in the present Embodiment Mode 4, an active matrix light-emitting device in which driving of light-emitting elements is controlled by transistors is described; however, the light-emitting device of the present invention may be a passive light-emitting device, as well. A perspective-view diagram of a passive matrix light-emitting device fabricated by application of the present invention is shown in FIGS. 8A and 8B. It is to be noted that FIG. 8A is a perspective-view diagram of the light-emitting device and FIG. 8B is a cross-sectional view of a cross section taken along X-Y in FIG. 8A. In FIGS. 8A and 8B, over a substrate 951, a layer 955 that includes a light-emitting layer is provided between an electrode 952 and an electrode 956. An edge of the electrode 952 is covered by an insulating layer 953. Partition wall layers 954 are provided over the insulating layer 953. Side walls of each of the partition wall layers 954 are slanted so that the distance from one side wall to the other side wall becomes narrower as the side walls are drawn closer to the surface of the substrate. That is, the cross section along the direction of the narrow side of each of the partition wall layers 954 is trapezoidal, where the bottom base (the side that comes into contact with the insulating layer 953 from the same direction as the surface direction of the insulating layer 953) of the trapezoid is shorter than the top base (the side that does not come into contact with the insulating layer 953 from the same direction as the surface direction of the insulating layer 953). In this way, by provision of the partition wall layers 954, defects in the light-emitting elements caused by static electricity or the like can be prevented.

Because the light-emitting device described in the present Embodiment Mode 4 is formed with the light-emitting element of the present invention, luminous efficacy is high and driving voltage is low. Consequently, the light-emitting device has the characteristic of low power consumption.

Embodiment Mode 5

Because a light-emitting device in which the light-emitting element of the present invention is used can display images of high quality, by application of the light-emitting device of the present invention in a display of an electronic device, an electronic device that displays images of superior quality can be obtained. Furthermore, because the luminous efficacy of the light-emitting device in which the light-emitting element of the present invention is included is high and driving voltage is low, the light-emitting device can be driven at low power consumption. Consequently, by application of the light-emitting device of the present invention to the display of an electronic device, an electronic device with low power consumption can be obtained; for example, a telephone set or the like that has a long standby time or the like can be obtained. Hereinafter, examples of modes of electronic devices in which is implemented a light-emitting device to which the light-emitting element of the present invention has been applied are given.

Figure 5A:
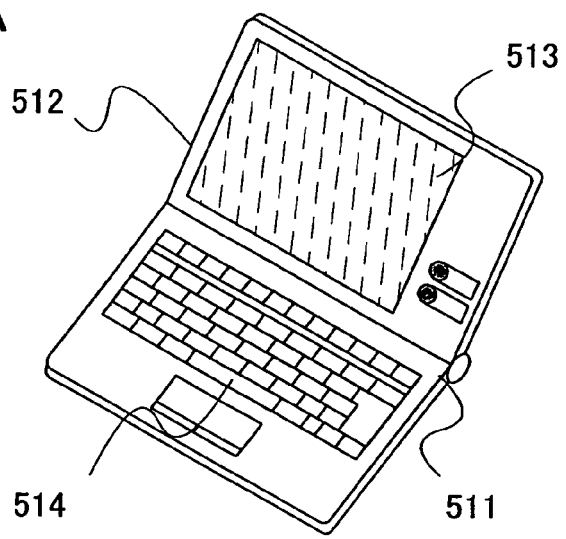
FIGS. 5A to 5C are diagrams used in the description of electronic devices in which the light-emitting devices of the present invention are used.

FIG. 5A is a diagram of a computer that is fabricated using the present invention and is formed of a main body 511, a chassis 512, a display 513, a keyboard 514, and the like. The computer can be completed by implementation of a light-emitting device that has the light-emitting element of the present invention for the display.

Figure 5B:
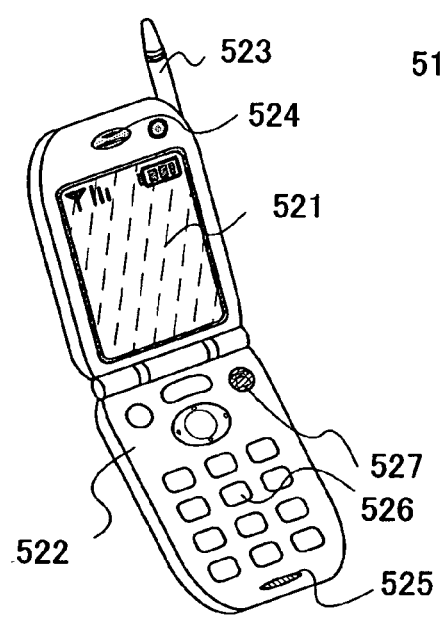

FIG. 5B is a diagram of a telephone set that is fabricated by application of the present invention and is formed of a display 521, an audio output 524, an audio input 525, operation switches 526 and 527, an antenna 523, and the like in a main body 522. The telephone set can be completed by implementation of a light-emitting device that has the light-emitting element of the present invention for the display.

Figure 5C:
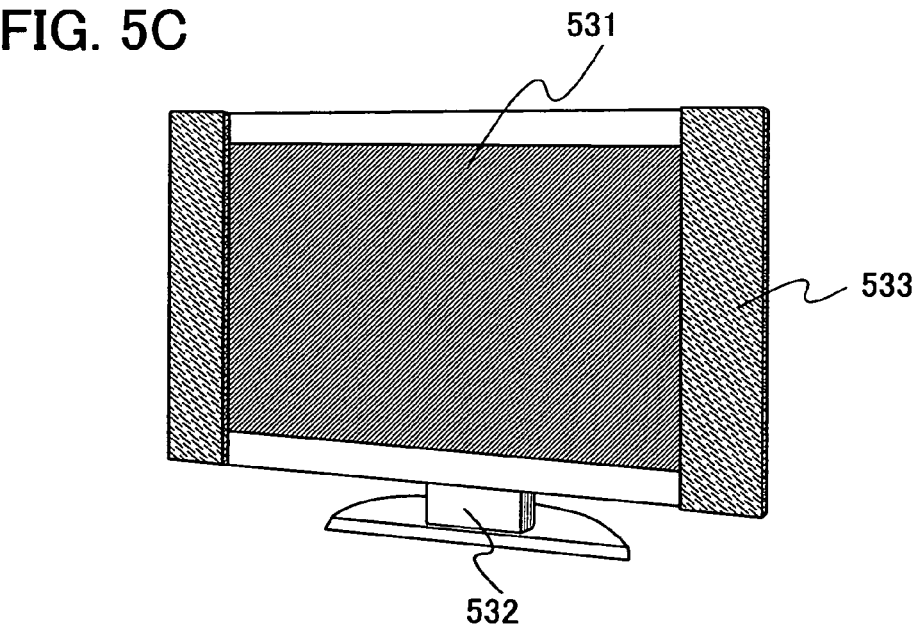

FIG. 5C is a diagram of a television set that is fabricated by application of the present invention and is formed of a display 531, a chassis 532, speakers 533, and the like. The television set can be completed by implementation of a light-emitting device that has the light-emitting element of the present invention for the display.

As described above, the light-emitting device of the present invention is extremely well-suited for use as a display of a variety of electronic devices.

It is to be noted that, in the present Embodiment Mode 5, a computer and the like are described, and in addition to the devices given above, a light-emitting device that has the light-emitting element of the present invention may be implemented in navigation devices, lighting equipment, and the like, as well.

Embodiment 1

Synthesis Example 1

In the present Synthesis Example 1, a synthesis example of the oxadiazole derivative, 2-[3-(carbazol-9-yl)phenyl]-5-phenyl-1,3,4-oxadiazole (abbreviated designation: mCO11), of the present invention that is represented by the Structural Formula (G1) of Embodiment Mode 1 will be presented in concrete terms.

Step 1: Synthesis of
2-(3-bromophenyl)-5-phenyl-1,3,4-oxadiazole
(abbreviated designation: mO11Br)

In the present Step 1, mO11Br was synthesized according to processes (i) to (iii) as given below.

(i) Synthesis of 3-bromobenzoylhydrazine

After 10 grams (44 mmol) of ethyl-3-bromobenzoate were placed into a 200 mL, three-neck flask, 50 mL of ethanol was added thereto and the mixture was stirred; 12 mL of hydrazine monohydrate was added, this mixture was stirred at 78° C. for 5 hours, and the contents of the flask were reacted together. After the reaction was completed, a solid was precipitated out with the addition of water to the reaction solution. The precipitate solid was removed by suction filtration. With the suction-filtered solid being placed into approximately 500 mL of water and washed and a solid removed by suction filtration, 8.1 grams of a white-colored solid, which was the objective of the synthesis process, were obtained at a yield of 86%.

(ii) Synthesis of
1-benzoyl-2-(3-bromobenzoyl)hydrazine

Next, 5.0 grams (23 mmol) of the 3-bromobenzoylhydrazine obtained in (i) were placed into a 300 mL, three-neck flask, 10 mL of N-methyl-2-pyrrolidone was added thereto, and the mixture was stirred. A mixed solution of 10 mL of N-methyl-2-pyrrolidone and 3.2 mL (28 mmol) of benzoyl chloride were dripped into this mixture through a 50 mL dropping funnel. After completion of the dripping, the mixture was heated and stirred at 80° C. for 3 hours, and the contents of the flask were reacted together. After the reaction was completed, a solid was precipitated out with the addition of water to the reaction solution. A solid was obtained by suction filtration of the precipitate solid. The obtained solid was washed with approximately 1 L of water and removed by suction filtration. After the suction-filtered solid was washed with methanol and a solid was removed by suction filtration, 7.1 grams of a white-colored solid, which was the objective of the synthesis process, were obtained at a yield of 96%.

(iii) Synthesis of mO11Br

Furthermore, 7.1 grams (22 mmol) of the 1-benzoyl-2-(3-bromobenzoyl)hydrazine obtained by the method described in (ii) above were placed into a 300-mL, three-neck flask; 100 mL of phosphoryl chloride was added thereto; the mixture was heated and stirred at 100° C. for 5 hours; and the contents of the flask were reacted together. After the reaction was completed, when the phosphoryl chloride in the flask was completely distilled away, a solid was obtained. The obtained solid was washed first with water and then with an aqueous solution of sodium carbonate, and an obtained solid was removed by suction filtration. When the removed solid was recrystallized by methanol, 4.9 grams of a white-colored solid, which was the objective of the synthesis process, were obtained at a yield of 73%. The synthesis scheme of the present Step 1 described above is shown in Scheme (a-1), which is given below.

[Chemical Formula 12: Scheme (a-1)]

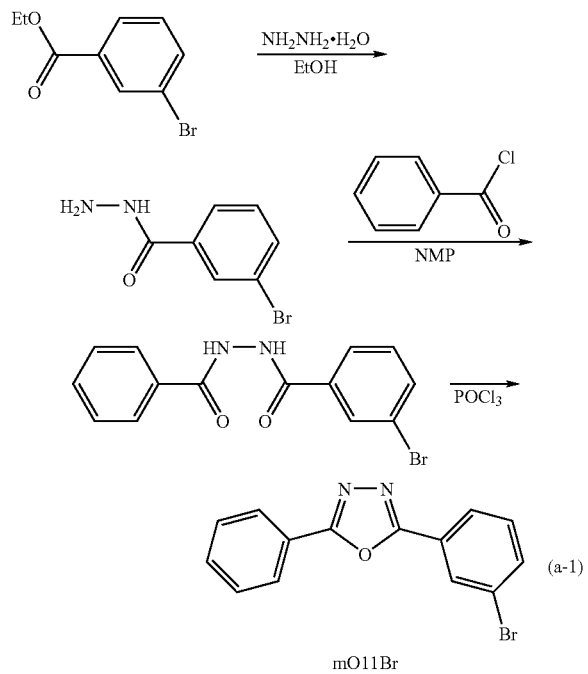

(a-1)

mO11Br

[Chemical Formula 13: Scheme (b-1)]

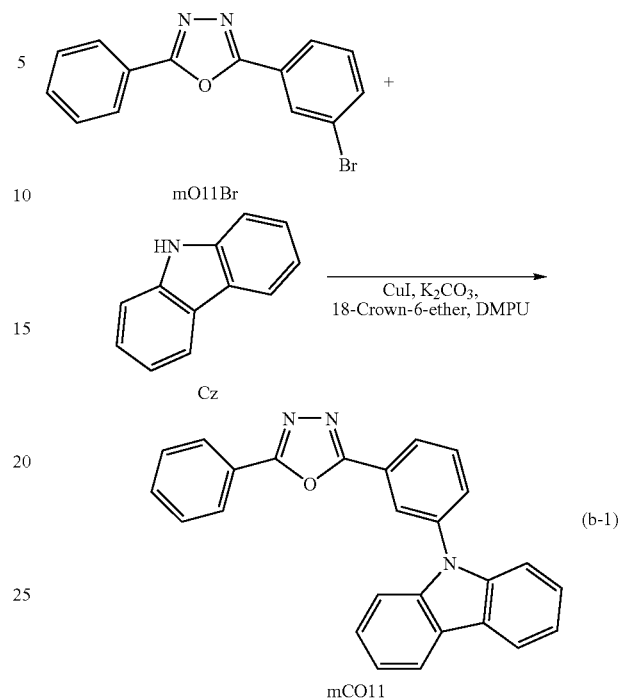

(b-1)

mCO11

Step 2: Synthesis of 2-[3-(carbazol-9-yl)phenyl]-5-phenyl-1,3,4-oxadiazole (abbreviated designation: mCO11)

1.9 g (6.6 mmol) of the mO11Br obtained in Step 1, 1.1 g (6.6 mmol) of carbazole, 3.0 g (22 mmol) of potassium carbonate, 0.30 g (1.6 mmol) of copper iodide, and 0.3 g (1.1 mmol) of 18-crown-6-ether were placed in a 50-mL, three-neck flask, and nitrogen substitution was performed on the contents of the flask. 3.0 mL of 1,3-dimethyl-3,4,5,6-tetrahydro-2(1H)-pyrimidinone (abbreviated designation: DMPU) were added to the mixture and heated and stirred at 180° C. for 5 hours, and the contents of the flask were reacted together. After the reaction was completed, toluene was added to the mixture. This suspension was washed with 1 N diluted hydrochloric acid, a saturated sodium carbonate solution, and a saturated saltwater solution, in the order given. An organic layer was dried with magnesium sulfate. Suction filtration was performed on this mixture to remove the magnesium sulfate, and a filtrate was obtained. Suction filtration was performed with sellite on the obtained filtrate, and a resulting filtrate was obtained. This obtained filtrate was condensed to obtain a solid. The obtained solid was purified by silica column chromatography. The column chromatography was performed first using toluene as a developing solvent and then using a mixed solvent of toluene:ethyl acetate=4:1 as a developing solvent. The obtained fraction was condensed to obtain a solid. When this solid was recrystallized with a mixed solvent of chloroform and hexane, 1.0 grams of a powdery, white-colored solid of mCO11, which was the objective of the Synthesis Example 1, were obtained at a yield of 50%. The synthesis scheme of the present Step 2 described above is shown in Scheme (b-1), which is given below.

Figure 6A:
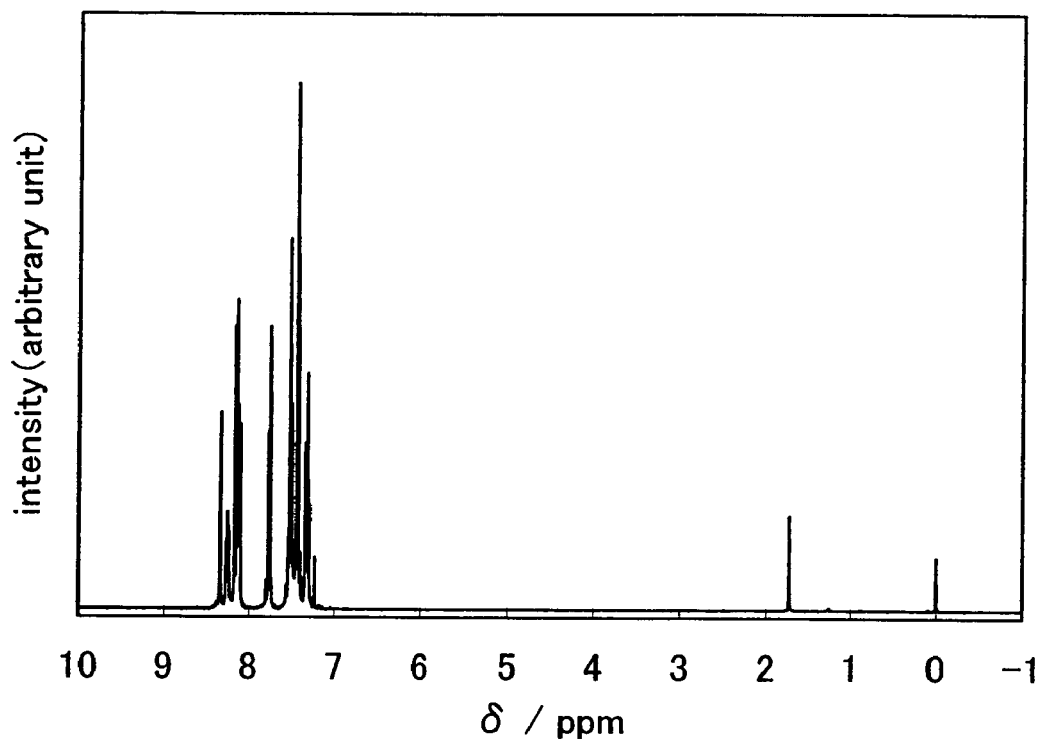
FIGS. 6A and 6B are diagrams showing $^1$H NMR spectra of the oxadiazole derivative mCO11 of the present invention.
Figure 6B:
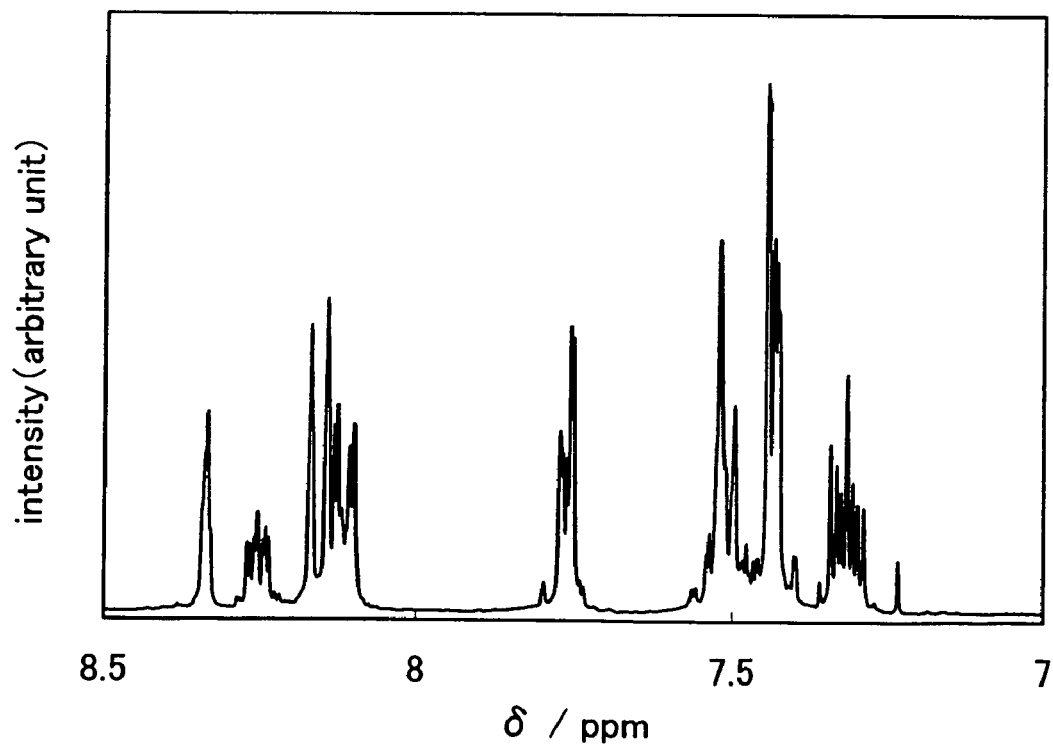

Analysis results obtained by nuclear magnetic resonance ($^1$H NMR) of the obtained mCO11 will be given hereinafter. In addition, an $^1$H NMR chart is shown in FIG. 6A, and an exploded view thereof is shown in FIG. 6B. From these charts, it was confirmed that the oxadiazole derivative mCO11 of the present invention that is represented by the Structural Formula (1) given above was obtained in the present Synthesis Example 1.

The $^1$H NMR data is given as follows. $^1$H NMR (CDCl$_3$, 300 MHz): δ=7.28-7.55 (m, 9H), 7.72-7.79 (m, 2H), 8.07-8.19 (m, 4H), 8.21-8.28 (m, 1H), and 8.34 (s, 1H).

Furthermore, sublimation purification of the obtained mCO11 was performed using a train sublimation method. Sublimation purification was performed at a reduced pressure of 7 Pa, with a flow rate of argon of 3 mL/min, at 215° C. for 15 hours. When sublimation purification was performed on 1.0 grams of mCO11, the yield was 0.80 grams of purified mCO11, which was a yield of 80%.

Figure 7A:
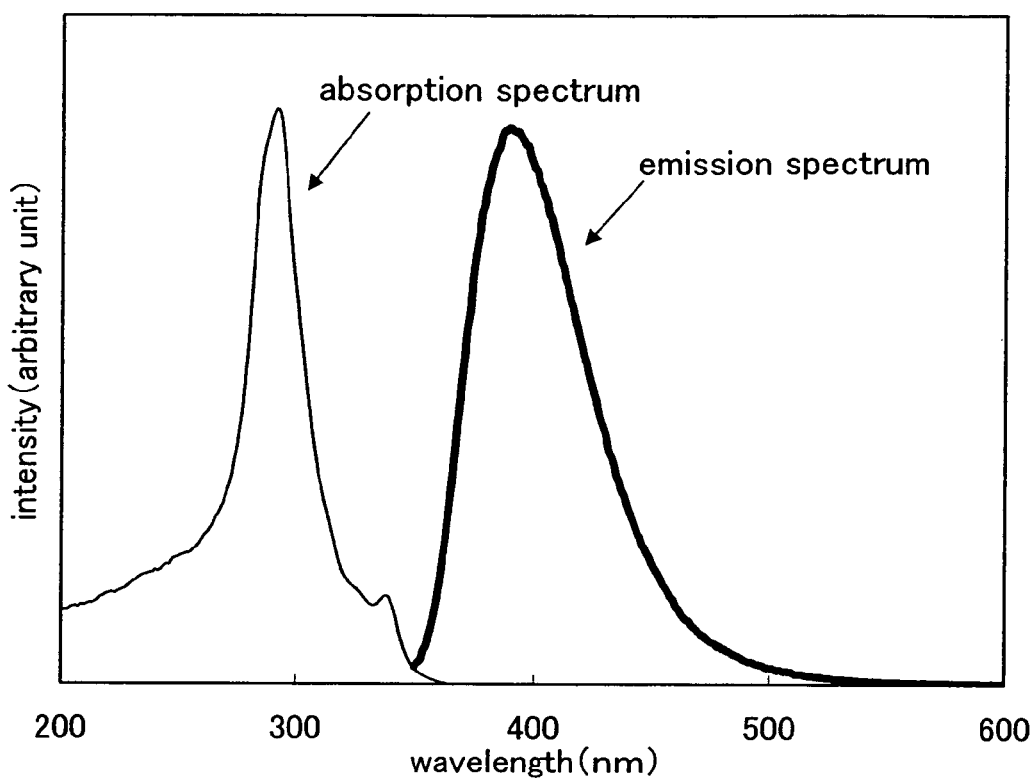
FIGS. 7A and 7B are diagrams showing ultraviolet and visible light absorption spectra and emission spectra of the oxadiazole derivative mCO11 of the present invention.
Figure 7B:
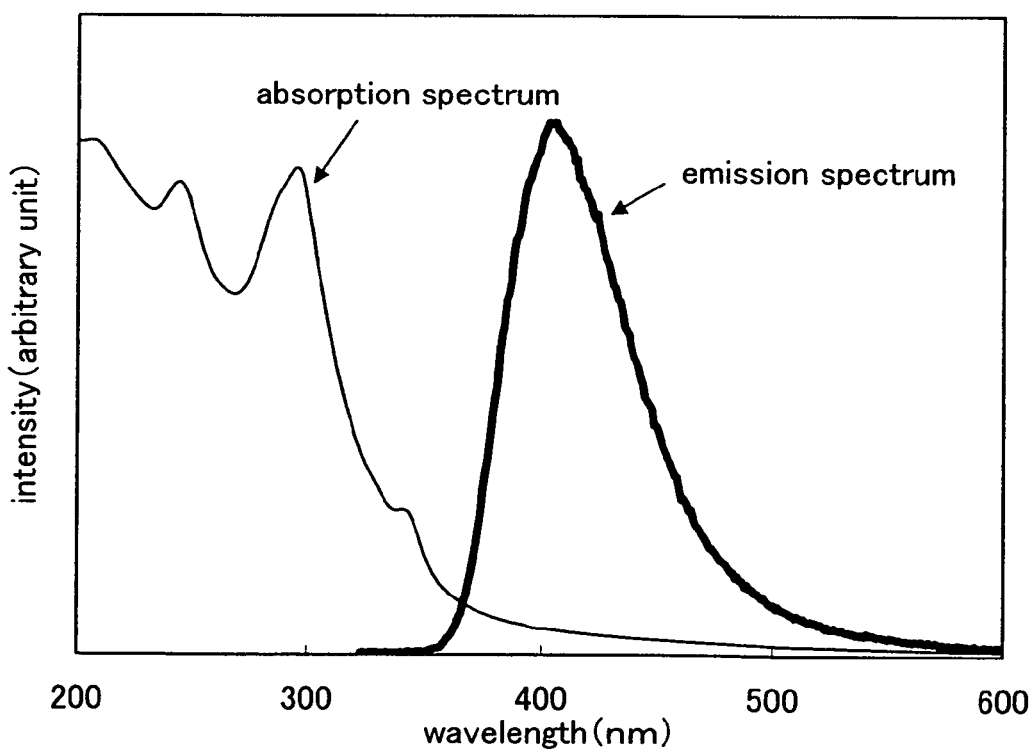

Next, the absorption spectra and emission spectra of mCO11 were measured. The absorption spectra were obtained using an ultraviolet-visible light spectrophotometer (V-550 series UV-VIS spectrophotometer manufactured by Jasco Inc.), and the emission spectra were obtained using a fluorimeter (FS920 fluorimeter manufactured by Hamamatsu Photonics K.K.). Measurements were performed in relation to a toluene solution and a deposited film, at room temperature. Measurement results for the toluene solution are shown in FIG. 7A, and those for the deposited film are shown in FIG. 7B. The horizontal axis represents wavelength, and the vertical axis represents the intensity of absorption and emission.

As shown in FIG. 7A, the toluene solution of the oxadiazole derivative mCO11 of the present invention has absorption peaks in the vicinities of 290 nm and 335 nm. Moreover, the emission spectrum has a peak at 390 nm. It is to be noted that the emission spectrum was measured by excitation at a wavelength of 290 nm.

Furthermore, as shown in FIG. 7B, the deposited film of oxadiazole derivative mCO11 of the present invention has absorption peaks in the vicinities of 244 nm, 295 nm, and 340 nm. In addition, the emission spectrum has a peak at 405 nm. It is to be noted that the emission spectrum was measured by excitation at a wavelength of 313 nm.

It is to be noted that the absorption edge was obtained by tauc plot of a direct transition using the absorption spectrum data of FIG. 7B, and the energy of the absorption edge was found to be 3.25 eV with the energy of the adsorption edge used as the energy gap of mCO11. From these results, it can be seen that the oxadiazole derivative mCO11 of the present invention has a high excitation energy.

Moreover, the result for the ionized potential of a thin film form of mCO11 measured using a photoelectron spectrometer (AC-2 photoelectron spectrometer manufactured by Riken Kikei, Co., Ltd.) at atmospheric pressure was 5.66 eV. As a result, it was understood that the HOMO level was −5.66 eV. Furthermore, the value of the LUMO level, derived from the energy gap obtained above and the HOMO level, was −2.41 eV.

In addition, the optimal molecular structure for the ground state of mCO11 was calculated by B3LYP/6-311 (d, p) of the density functional theory (DFT). The DFT was employed for the present calculation because the degree of accuracy for calculation is higher compared to that of the Hartree-Fock (HF) method and calculation costs are lower compared to those of the method of perturbation (MP), which has the same level of accuracy for calculation as the DFT. The calculations were performed using a high performance computer (HPC) (Altix 3700 DX supercomputer manufactured by SGI). When the singlet excitation energy of mCO11 was calculated by application of B3LYP/6-311 (d, p) of the time-dependent density functional theory (TDDFT) in the molecular structure that was structurally optimized by DFT, the singlet excitation energy was found to be 3.13 eV. Furthermore, when the singlet excitation energy of mCO11 was calculated, it was found to be 2.83 eV. From the above results, it can be seen that the oxadiazole derivative mCO11 of the present invention has a high excitation energy. In particular, it can be seen that the oxadiazole derivative mCO11 of the present invention has a high triplet excitation energy.

This application is based on Japanese Patent Application serial no. 2007-072624 filed with the Japan Patent Office on Mar. 20, 2007, the entire contents of which are hereby incorporated by reference.

What is claimed is:

1. A light-emitting element comprising:
an anode and a cathode;
a light-emitting layer; and
an exciton blocking layer between the anode and the light-emitting layer,
wherein the exciton blocking layer is in contact with the light-emitting layer,
wherein the exciton blocking layer comprises an oxadiazole derivative represented by General Formula (G1):

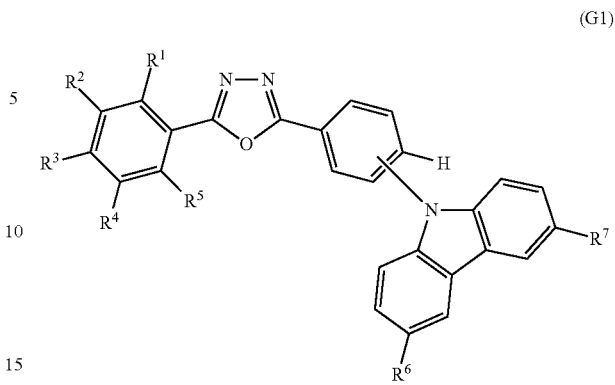

wherein $R^1$ to $R^5$ each represents either hydrogen or an alkyl group with from 1 to 4 carbon atoms, and $R^6$ and $R^7$ each represents an alkyl group with from 1 to 4 carbon atoms.

2. The light-emitting element according to claim 1, wherein the light-emitting layer comprises a host material and a guest material.

3. The light-emitting element according to claim 1, further comprising:
a hole-injection layer and a hole-transporting layer between the anode and the exciton blocking layer.

4. A light-emitting device,
wherein the light-emitting device comprises the light-emitting element according to claim 1.

5. The light-emitting element according to claim 1, further comprising:
an electron-transporting layer and an electron-injection layer between the light-emitting layer and the cathode.

6. A light-emitting element comprising:
an anode and a cathode;
a light-emitting layer; and
an exciton blocking layer between the cathode and the light-emitting layer,
wherein the exciton blocking layer is in contact with the light-emitting layer,
wherein the exciton blocking layer comprises an oxadiazole derivative represented by General Formula (G1):

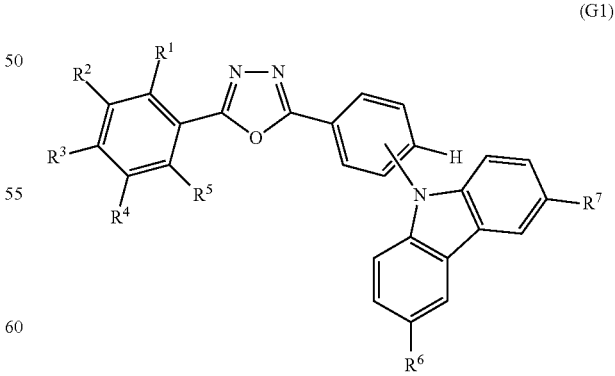

wherein $R^1$ to $R^5$ each represents either hydrogen or an alkyl group with from 1 to 4 carbon atoms, and $R^6$ and $R^7$ each represents an alkyl group with from 1 to 4 carbon atoms.

7. The light-emitting element according to claim 6,
wherein the light-emitting layer comprises a host material and a guest material.

8. The light-emitting element according to claim 6, further comprising:
a hole-injection layer and a hole-transporting layer between the anode and the exciton blocking layer.

9. A light-emitting device,
wherein the light-emitting device comprises the light-emitting element according to claim 6.

10. The light-emitting element according to claim 6, further comprising:
an electron-transporting layer and an electron-injection layer between the light-emitting layer and the cathode.

11. The light-emitting element according to claim 1, wherein the oxadiazole derivative has any one of the structural formulae (9)-(12):

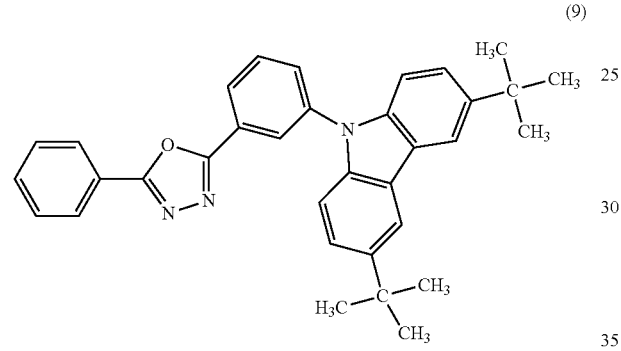

(9)

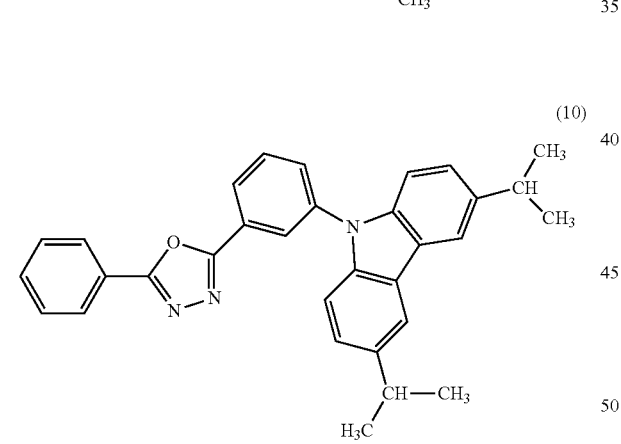

(10)

(11)

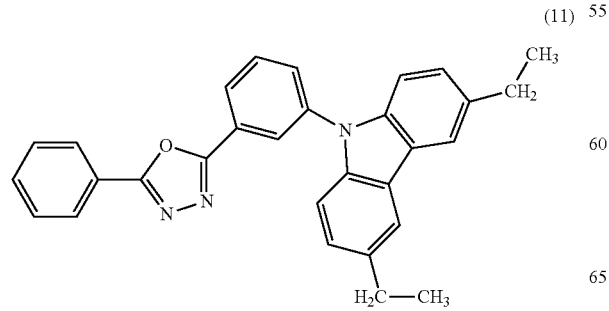

-continued

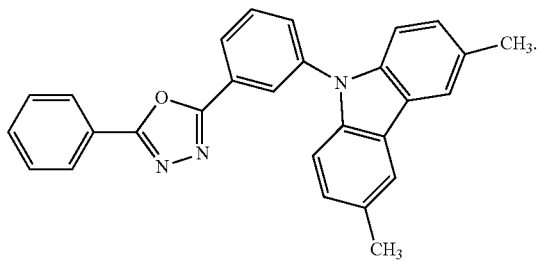

(12)

12. The light-emitting element according to claim 1, wherein the oxadiazole derivative has any one of the structural formulae (19)-(22):

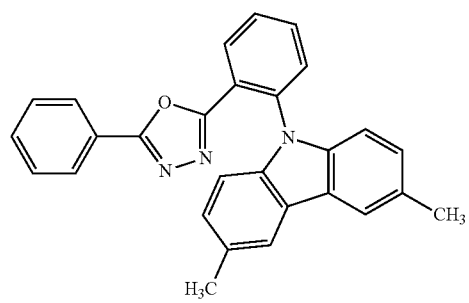

(19)

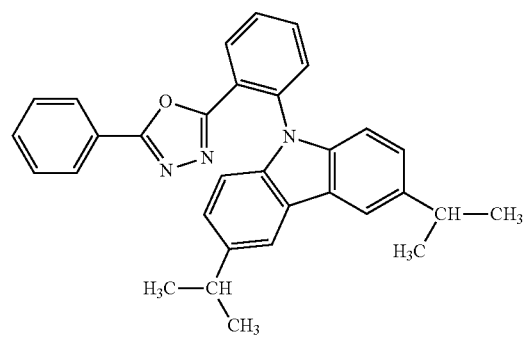

(20)

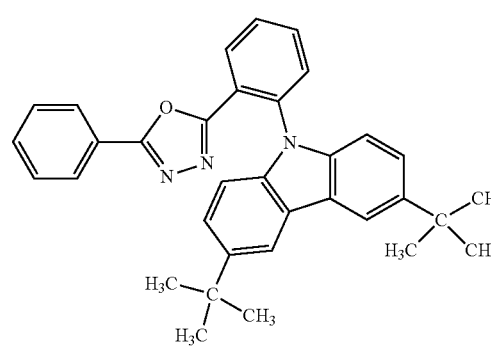

(21)

(22)
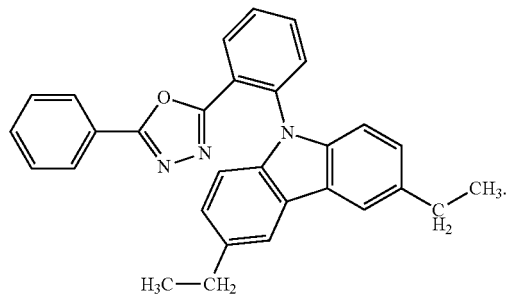
(12)
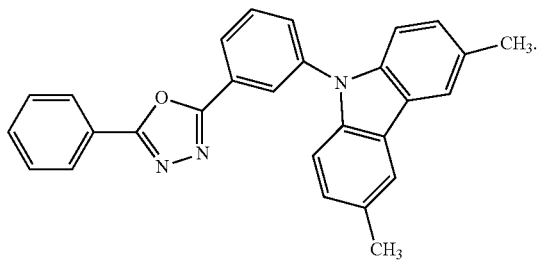
13. The light-emitting element according to claim 6, wherein the oxadiazole derivative has any one of the structural formulae (9)-(12):
14. The light-emitting element according to claim 6, wherein the oxadiazole derivative has any one of the structural formulae (19)-(22):
(9)
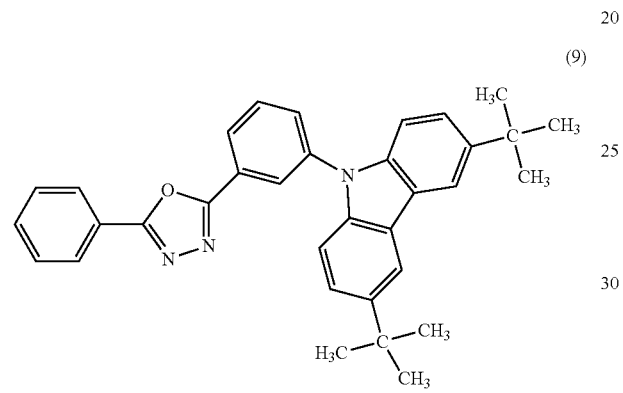
(19)
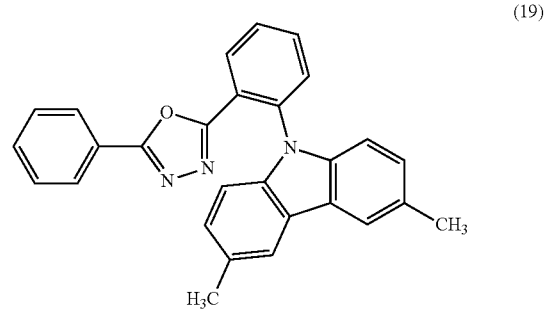
(10)
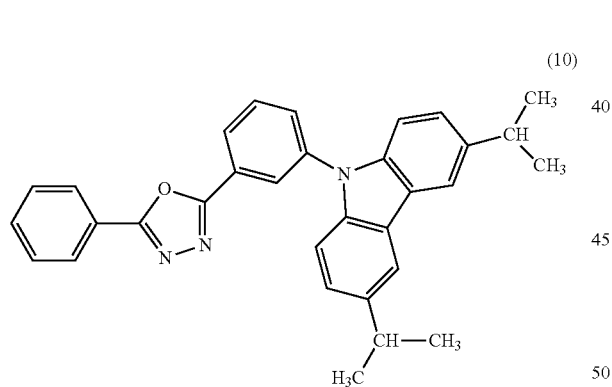
(20)
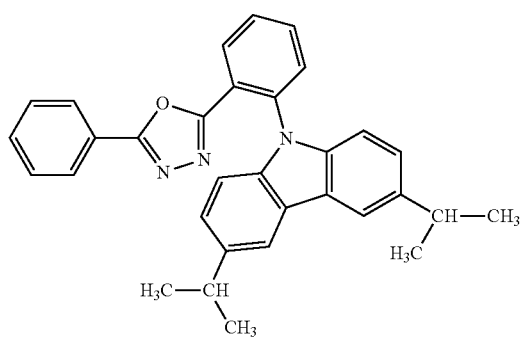
(11)
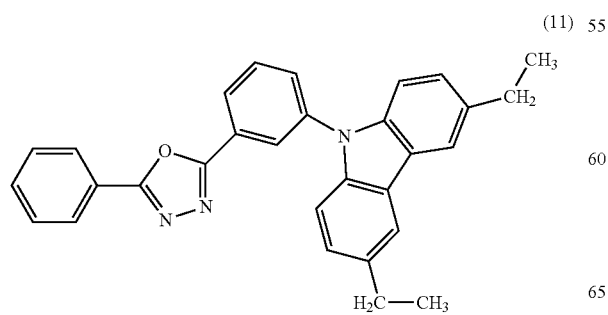
(21)
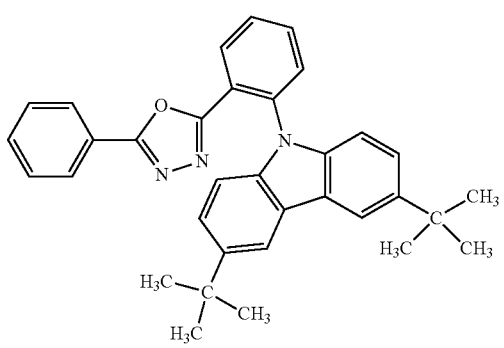

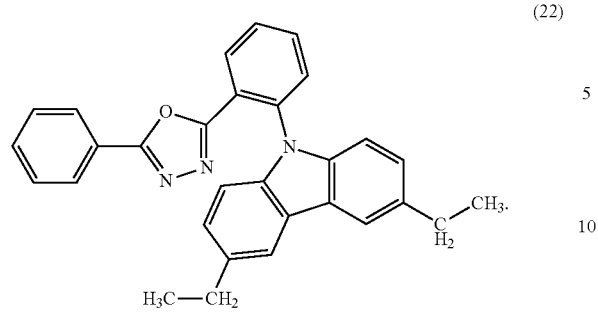
(22)